US008298831B2

(12) United States Patent
Nolte et al.

(10) Patent No.: US 8,298,831 B2
(45) Date of Patent: Oct. 30, 2012

(54) DIFFERENTIALLY ENCODED BIOLOGICAL ANALYZER PLANAR ARRAY APPARATUS AND METHODS

(75) Inventors: David D. Nolte, Lafayette, IN (US); Manoj Varma, West Lafayette, IN (US); Fred E. Regnier, West Lafayette, IN (US); Leilei Peng, West Lafayette, IN (US); Ming Zhao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 72 days.

(21) Appl. No.: 12/466,943

(22) Filed: May 15, 2009

(65) Prior Publication Data
US 2009/0263913 A1 Oct. 22, 2009

Related U.S. Application Data

(62) Division of application No. 11/345,566, filed on Feb. 1, 2006, now abandoned.

(60) Provisional application No. 60/648,724, filed on Feb. 1, 2005.

(51) Int. Cl.
*G01N 21/76* (2006.01)
(52) U.S. Cl. ........ 436/172; 356/450; 356/456; 436/164; 436/518; 435/4; 435/287.1
(58) Field of Classification Search .................. None
See application file for complete search history.

(56) References Cited

U.S. PATENT DOCUMENTS

| | | | |
|---|---|---|---|
| 3,796,495 A | 3/1974 | Laub | |
| 4,537,861 A | 8/1985 | Elings et al. | |
| 4,741,620 A | 5/1988 | Wickramasinghe | |

(Continued)

FOREIGN PATENT DOCUMENTS

EP 1189062 A1 3/2002
(Continued)

OTHER PUBLICATIONS

Abe, Takao, et al., Microroughness Measurements on Polished Silicon Wafers, Jpn. 31, pp. 721-728, 1992.
(Continued)

*Primary Examiner* — N. C. Yang
(74) *Attorney, Agent, or Firm* — Faegre Baker Daniels LLP

(57) ABSTRACT

A method of probing a plurality of analyzer molecules distributed about a detection platform is disclosed. The method includes contacting a test sample to the plurality of analyzer molecules, scanning the plurality of analyzer molecules at a rate relating to a carrier frequency signal, and detecting the presence or absence of a biological molecule based at least in part upon the presence or absence of a signal substantially at a sideband of the carrier frequency signal. A molecule detection platform including a substrate and a plurality of targets positioned about the substrate is also disclosed. Specific analyzer molecules adapted to bind a specific analyte are immobilized about a first set of the targets. Nonspecific analyzer molecules are immobilized about a second set of the targets. The targets positioned about the substrate along at least a segment of a scanning pathway alternate between at least one of the first set and at least one of the second set. A method including providing a substrate for supporting biological analyzer molecules the substrate including at least one scanning pathway is also disclosed. The scanning pathway includes a plurality of scanning targets. Specific biological analyzer molecules adapted to detect a specific target analyte are distributed about a first set of the targets which alternate in groups of at least one with a second set of the targets the second set of the targets not including the specific biological analyzer molecules.

9 Claims, 28 Drawing Sheets
(5 of 28 Drawing Sheet(s) Filed in Color)

U.S. PATENT DOCUMENTS

| | | |
|---|---|---|
| 4,876,208 A | 10/1989 | Gustafson et al. |
| 4,899,195 A | 2/1990 | Gotoh |
| 4,975,217 A | 12/1990 | Brown |
| RE33,581 E | 4/1991 | Nicoli et al. |
| 5,122,284 A | 6/1992 | Braynin et al. |
| 5,155,549 A | 10/1992 | Dhadwal |
| 5,413,939 A | 5/1995 | Gustafson et al. |
| 5,478,527 A | 12/1995 | Gustafson et al. |
| 5,478,750 A | 12/1995 | Bernstein et al. |
| 5,494,829 A | 2/1996 | Sandstrom et al. |
| 5,497,007 A | 3/1996 | Uritsky et al. |
| 5,545,531 A | 8/1996 | Rava et al. |
| 5,581,345 A | 12/1996 | Oki et al. |
| 5,602,377 A | 2/1997 | Beller et al. |
| 5,621,532 A | 4/1997 | Ooki et al. |
| 5,629,044 A | 5/1997 | Rubenchik |
| 5,631,171 A | 5/1997 | Sandstrom et al. |
| 5,653,939 A | 8/1997 | Hollis et al. |
| 5,700,046 A | 12/1997 | Van Doren et al. |
| 5,717,778 A | 2/1998 | Chu et al. |
| 5,736,257 A | 4/1998 | Conrad et al. |
| 5,781,649 A | 7/1998 | Brezoczky |
| 5,786,226 A | 7/1998 | Bocker et al. |
| 5,837,475 A | 11/1998 | Dorsel et al. |
| 5,843,767 A | 12/1998 | Beattie |
| 5,844,871 A | 12/1998 | Maezawa |
| 5,874,219 A | 2/1999 | Rava et al. |
| 5,875,029 A | 2/1999 | Jann et al. |
| 5,883,717 A | 3/1999 | DiMarzio et al. |
| 5,892,577 A | 4/1999 | Gordon |
| 5,900,935 A | 5/1999 | Klein et al. |
| 5,922,617 A | 7/1999 | Wang et al. |
| 5,935,785 A | 8/1999 | Reber et al. |
| 5,945,334 A | 8/1999 | Besemer et al. |
| 5,945,344 A | 8/1999 | Hayes et al. |
| 5,955,377 A | 9/1999 | Maul et al. |
| 5,968,728 A | 10/1999 | Perttunen et al. |
| 5,999,262 A | 12/1999 | Dobschal et al. |
| 6,008,892 A | 12/1999 | Kain et al. |
| 6,030,581 A | 2/2000 | Virtanen |
| 6,048,692 A | 4/2000 | Maracas et al. |
| 6,060,237 A | 5/2000 | Nygren et al. |
| 6,071,748 A | 6/2000 | Modlin et al. |
| 6,099,803 A | 8/2000 | Ackley |
| 6,110,748 A | 8/2000 | Reber et al. |
| 6,121,048 A | 9/2000 | Zaffaroni et al. |
| 6,140,044 A | 10/2000 | Besemer et al. |
| 6,143,247 A | 11/2000 | Sheppard |
| 6,177,990 B1 | 1/2001 | Kain et al. |
| 6,221,579 B1 | 4/2001 | Everhart et al. |
| 6,238,869 B1 | 5/2001 | Kris et al. |
| 6,248,539 B1 | 6/2001 | Ghadiri et al. |
| 6,249,593 B1 | 6/2001 | Chu et al. |
| 6,256,088 B1 | 7/2001 | Gordon |
| 6,271,924 B1 | 8/2001 | Ngoi et al. |
| 6,287,783 B1 | 9/2001 | Maynard et al. |
| 6,287,850 B1 | 9/2001 | Besemer et al. |
| 6,312,901 B2 | 11/2001 | Virtanen |
| 6,312,961 B1 | 11/2001 | Voirin et al. |
| 6,319,468 B1 | 11/2001 | Sheppard, Jr. et al. |
| 6,319,469 B1 | 11/2001 | Mian et al. |
| 6,320,665 B1 | 11/2001 | Ngoi et al. |
| 6,327,031 B1 | 12/2001 | Gordon |
| 6,339,473 B1 | 1/2002 | Gordon |
| 6,342,349 B1 | 1/2002 | Virtanen |
| 6,342,395 B1 | 1/2002 | Hammock et al. |
| 6,345,115 B1 | 2/2002 | Ramm et al. |
| 6,350,413 B1 | 2/2002 | Reichert et al. |
| 6,355,429 B1 | 3/2002 | Nygren et al. |
| 6,368,795 B1 | 4/2002 | Hefti |
| 6,376,258 B2 | 4/2002 | Hefti |
| 6,381,025 B1 | 4/2002 | Bornhop et al. |
| 6,387,331 B1 | 5/2002 | Hunter |
| 6,395,558 B1 | 5/2002 | Duveneck et al. |
| 6,395,562 B1 | 5/2002 | Hammock et al. |
| 6,399,365 B2 | 6/2002 | Besemer et al. |
| 6,403,957 B1 | 6/2002 | Fodor et al. |
| 6,416,642 B1 | 7/2002 | Alajoki et al. |
| 6,469,787 B1 | 10/2002 | Meyer et al. |
| 6,476,907 B1 | 11/2002 | Gordon |
| 6,483,585 B1 | 11/2002 | Yang |
| 6,483,588 B1 | 11/2002 | Graefe et al. |
| 6,496,267 B1 | 12/2002 | Takaoka |
| 6,496,309 B1 | 12/2002 | Bliton et al. |
| 6,504,618 B2 | 1/2003 | Morath et al. |
| 6,518,056 B2 | 2/2003 | Schembri et al. |
| 6,551,817 B2 | 4/2003 | Besemer et al. |
| 6,566,069 B2 | 5/2003 | Virtanen |
| 6,584,217 B1 | 6/2003 | Lawless et al. |
| 6,591,196 B1 | 7/2003 | Yakhini et al. |
| 6,596,483 B1 | 7/2003 | Choong et al. |
| 6,602,702 B1 | 8/2003 | McDevitt et al. |
| 6,623,696 B1 | 9/2003 | Kim et al. |
| 6,624,896 B1 | 9/2003 | Neal et al. |
| 6,649,403 B1 | 11/2003 | McDevitt |
| 6,653,152 B2 | 11/2003 | Challener |
| 6,656,428 B1 | 12/2003 | Clark et al. |
| 6,685,885 B2 | 2/2004 | Nolte et al. |
| 6,687,008 B1 | 2/2004 | Peale et al. |
| 6,709,869 B2 | 3/2004 | Mian et al. |
| 6,720,177 B2 | 4/2004 | Ghadiri et al. |
| 6,733,977 B2 | 5/2004 | Besemer et al. |
| 6,734,000 B2 | 5/2004 | Bhatia |
| 6,737,238 B2 | 5/2004 | Suzuki |
| 6,743,633 B1 | 6/2004 | Hunter |
| 6,760,298 B2 | 7/2004 | Worthington et al. |
| 6,766,817 B2 | 7/2004 | da Silva |
| 6,770,447 B2 | 8/2004 | Maynard et al. |
| 6,783,938 B2 | 8/2004 | Nygren et al. |
| 6,787,110 B2 | 9/2004 | Tiefenthaler |
| 6,791,677 B2 | 9/2004 | Kawai et al. |
| 6,803,999 B1 | 10/2004 | Gordon |
| 6,806,963 B1 | 10/2004 | Walti et al. |
| 6,819,432 B2 | 11/2004 | Pepper et al. |
| 6,836,338 B2 | 12/2004 | Opsal et al. |
| 6,844,965 B1 | 1/2005 | Engelhardt |
| 6,847,452 B2 | 1/2005 | Hill |
| 6,878,555 B2 | 4/2005 | Andersson et al. |
| 6,897,965 B2 | 5/2005 | Ghadiri et al. |
| 6,917,421 B1 | 7/2005 | Wihl et al. |
| 6,917,432 B2 | 7/2005 | Hill et al. |
| 6,918,404 B2 | 7/2005 | da Silva |
| 6,937,323 B2 | 8/2005 | Worthington et al. |
| 6,955,878 B2 | 10/2005 | Kambara et al. |
| 6,958,131 B2 | 10/2005 | Tiefenthaler |
| 6,980,299 B1 | 12/2005 | de Boer |
| 6,980,677 B2 | 12/2005 | Niles et al. |
| 6,987,569 B2 | 1/2006 | Hill |
| 6,990,221 B2 | 1/2006 | Shams |
| 6,992,769 B2 | 1/2006 | Gordon |
| 6,995,845 B2 | 2/2006 | Worthington |
| 7,006,927 B2 | 2/2006 | Yakhini et al. |
| 7,008,794 B2 | 3/2006 | Goh et al. |
| 7,012,249 B2 | 3/2006 | Krutchinsky et al. |
| 7,014,815 B1 | 3/2006 | Worthington et al. |
| 7,026,131 B2 | 4/2006 | Hurt et al. |
| 7,027,163 B2 | 4/2006 | Angeley |
| 7,031,508 B2 | 4/2006 | Lawless et al. |
| 7,033,747 B2 | 4/2006 | Gordon |
| 7,042,570 B2 | 5/2006 | Sailor |
| 7,061,594 B2 | 6/2006 | Worthington et al. |
| 7,066,586 B2 | 6/2006 | da Silva |
| 7,070,987 B2 | 7/2006 | Cunningham et al. |
| 7,077,996 B2 | 7/2006 | Randall et al. |
| 7,083,920 B2 | 8/2006 | Werner et al. |
| 7,087,203 B2 | 8/2006 | Gordon et al. |
| 7,088,650 B1 | 8/2006 | Worthington et al. |
| 7,091,034 B2 | 8/2006 | Virtanen |
| 7,091,049 B2 | 8/2006 | Boga et al. |
| 7,094,595 B2 | 8/2006 | Cunningham et al. |
| 7,094,609 B2 | 8/2006 | Demers |
| 7,098,041 B2 | 8/2006 | Kaylor et al. |
| 7,102,752 B2 | 9/2006 | Kaylor et al. |
| 7,106,513 B2 | 9/2006 | Moon et al. |
| 7,110,094 B2 | 9/2006 | Gordon |
| 7,110,345 B2 | 9/2006 | Worthington et al. |
| 7,118,855 B2 | 10/2006 | Cohen et al. |

| | | |
|---|---|---|
| 7,141,378 B2 | 11/2006 | Miller et al. |
| 7,141,416 B2 | 11/2006 | Krutzik |
| 7,145,645 B2 | 12/2006 | Blumenfeld et al. |
| 7,148,970 B2 | 12/2006 | de Boer |
| 7,200,088 B2 | 4/2007 | Worthington et al. |
| 7,221,632 B2 | 5/2007 | Worthington et al. |
| 7,312,046 B2 | 12/2007 | Chin |
| 7,318,903 B2 | 1/2008 | Link |
| 2001/0055812 A1 | 12/2001 | Mian et al. |
| 2002/0001546 A1 | 1/2002 | Hunter et al. |
| 2002/0008871 A1 | 1/2002 | Poustka et al. |
| 2002/0045276 A1 | 4/2002 | Yguerabide et al. |
| 2002/0051973 A1 | 5/2002 | Delenstarr et al. |
| 2002/0058242 A1 | 5/2002 | Demers |
| 2002/0085202 A1 | 7/2002 | Gordon |
| 2002/0097658 A1 | 7/2002 | Worthington et al. |
| 2002/0106661 A1 | 8/2002 | Virtanen et al. |
| 2002/0127565 A1 | 9/2002 | Cunningham et al. |
| 2002/0135754 A1 | 9/2002 | Gordon |
| 2002/0151043 A1 | 10/2002 | Gordon |
| 2002/0177144 A1* | 11/2002 | Remacle et al. .......... 435/6 |
| 2002/0192664 A1 | 12/2002 | Nygren et al. |
| 2003/0026735 A1 | 2/2003 | Nolte et al. |
| 2003/0035352 A1 | 2/2003 | Worthington |
| 2003/0054376 A1 | 3/2003 | Mullis et al. |
| 2003/0112446 A1 | 6/2003 | Miller et al. |
| 2003/0133640 A1 | 7/2003 | Tiefenthaler |
| 2003/0134330 A1 | 7/2003 | Ravkin et al. |
| 2004/0002085 A1 | 1/2004 | Schembri et al. |
| 2004/0078337 A1 | 4/2004 | King et al. |
| 2004/0086929 A1* | 5/2004 | Weide et al. .......... 435/6 |
| 2004/0106130 A1 | 6/2004 | Besemer et al. |
| 2004/0132172 A1 | 7/2004 | Cunningham et al. |
| 2004/0150829 A1 | 8/2004 | Koch et al. |
| 2004/0155309 A1 | 8/2004 | Sorin |
| 2004/0166525 A1 | 8/2004 | Besemer et al. |
| 2004/0166593 A1 | 8/2004 | Nolte et al. |
| 2004/0223881 A1 | 11/2004 | Cunningham et al. |
| 2004/0229254 A1 | 11/2004 | Clair |
| 2004/0247486 A1 | 12/2004 | Tiefenthaler |
| 2004/0258927 A1 | 12/2004 | Conzone et al. |
| 2005/0002827 A1 | 1/2005 | McIntyre et al. |
| 2005/0003459 A1 | 1/2005 | Krutzik |
| 2005/0019901 A1 | 1/2005 | Matveeva et al. |
| 2005/0042628 A1 | 2/2005 | Rava et al. |
| 2005/0084422 A1 | 4/2005 | Kido et al. |
| 2005/0084895 A1 | 4/2005 | Besemer et al. |
| 2005/0106746 A1 | 5/2005 | Shinn et al. |
| 2005/0123907 A1 | 6/2005 | Rava et al. |
| 2005/0131745 A1 | 6/2005 | Keller et al. |
| 2005/0158819 A1 | 7/2005 | Besemer et al. |
| 2005/0176058 A1 | 8/2005 | Zaffaroni et al. |
| 2005/0191630 A1 | 9/2005 | Besemer et al. |
| 2005/0214950 A1 | 9/2005 | Roeder et al. |
| 2005/0226769 A1 | 10/2005 | Shiga |
| 2005/0248754 A1 | 11/2005 | Wang et al. |
| 2005/0254062 A1 | 11/2005 | Tan et al. |
| 2005/0259260 A1 | 11/2005 | Wakita |
| 2006/0040380 A1 | 2/2006 | Besemer et al. |
| 2006/0078935 A1 | 4/2006 | Werner et al. |
| 2006/0204399 A1 | 9/2006 | Freeman et al. |
| 2006/0210449 A1 | 9/2006 | Zoval et al. |
| 2006/0223172 A1 | 10/2006 | Bedingham et al. |
| 2006/0234267 A1 | 10/2006 | Besemer et al. |
| 2006/0256350 A1 | 11/2006 | Nolte et al. |
| 2006/0256676 A1 | 11/2006 | Nolte et al. |
| 2006/0257939 A1 | 11/2006 | Demers |
| 2006/0269450 A1 | 11/2006 | Kim et al. |
| 2006/0270064 A1 | 11/2006 | Gordon et al. |
| 2007/0003436 A1 | 1/2007 | Nolte et al. |
| 2007/0003925 A1 | 1/2007 | Nolte et al. |
| 2007/0003979 A1 | 1/2007 | Worthington |
| 2007/0023643 A1 | 2/2007 | Nolte et al. |
| 2007/0070848 A1 | 3/2007 | Worthington et al. |
| 2007/0077599 A1 | 4/2007 | Krutzik |
| 2007/0077605 A1 | 4/2007 | Hurt et al. |
| 2007/0108465 A1 | 5/2007 | Pacholski |

FOREIGN PATENT DOCUMENTS

| | | |
|---|---|---|
| EP | 1424549 | 6/2004 |
| WO | WO 9104489 | 4/1991 |
| WO | WO 9104491 | 4/1991 |
| WO | WO 9113353 | 9/1991 |
| WO | WO 9214136 | 8/1992 |
| WO | WO 9403774 | 2/1994 |
| WO | WO 9837238 | 2/1998 |
| WO | WO 0000265 | 1/2000 |
| WO | WO 0039584 | 7/2000 |
| WO | WO 0111310 | 2/2001 |
| WO | WO 0144441 | 6/2001 |
| WO | WO 03014711 A1 | 2/2003 |
| WO | WO 2006042746 | 4/2006 |
| WO | WO 2006/075797 A1 | 7/2006 |

OTHER PUBLICATIONS

S. Balassubramanian, L.Lahiri, Y. Ding, M.R. Melloch, and D.D. Nolte, Two-Wave Mixing Dynamics and Nonlinear Hot-Electron Transport in Transverse-Geometry Photorefractive Quantum Wells Studies by Moving Grantings, Appl. Phys. B. 68, pp. 863-9 (1990).
Bietsch, A. and B. Michel, Conformal Contact and Pattern Stability of Stamps Used for Soft Lithography, J. Appl. Phys., 2000, vol. 88, pp. 4310-4318.
Brecht, A. and Gauglitz, G., Recent Developments in Optical Transducers for Chemical or Biochemical Applications. Sensors and Actuators B, 1997 vol. 38-39, pp. 1-7.
E. Delmarche, A. Bernard, H. Schmid, B. Michel, and H. Biebuyck, Patterned Delivery of Immunoglobulins to Surface Using Microfluidic Networks, Science 276,779-781(1997).
E. Delamarche, A. Bernard, Schmid, B., Bietsch, Michel, and H. Biebuyck, Microfluidic Networks for Chemical Patterning of Substrates: Design and Application to Bioassays, Journal of the American Chemical Society 120, pp. 500-508 (1998).
A. Blouin et al., Detection of Ultrasonic Motion of a Scattering Surface by Two-Wave Mixing in a Photorefractive GaAs Crystal, Appl. Phys. Lett. 65, pp. 932-934 (1994).
P. Delaye, A. Blouin, D. Drolet, L.A. Montmorrillong, A. Roosen, and J.P. MONCHAL1N, Detection of Ultrasonic Motion of a Scattering Surface by Photorefractive InP:Fe Under an Applied dc Field, J. Opt. Soc. Am. B14, pp. 1723-34 (1997).
Ding, Y. et al., Femtosecond Pulse Shaping by Dynamic Holograms in Photorefractive Multiple Quantum Wells, Optical Society of America, Optics Letters, vol. 22, pp. 718-720, 1997.
Ding, Y. et al., Adaptive All-Order Dispersion Compensation of Ultrafast Laser Pulses Using Dynamic Spectral Holography, American Institute of Physics, Applied Physics Letters, vol. 77, pp. 3255-3257, 1999.
DuBendorfer, J. and Kunz, R. E., Reference Pads for Miniature Integrated Optical Sensors. Sensors and Actuators B, 1997, vol. 38-39, pp. 116-121.
Effenhauser, C.S., et al., Integrated Capillary Electrophoresis on Flexible Silicone Microdevices: Analysis of DNA Restriction Fragments and Detection of Single DNA Molecules on Microchips. Anal. Chem., 1997, vol. 69, pp. 3451-3457.
Ekins, R., F. Chu and E. Biggart, Development of Microspot Multi-Analyte Ratiometric Immunoassay Using Dual Flourescent-Labelled Antibodies. Anal. Chim. Acta, 1989, vol. 227, pp. 73-96.
Ekins R et al. Multianalyte Microspot Immunoassay, The Microanalytical Compact Disk of the Future: Clin. Chem., 1991, Vo. 37(11), p. 1955-1967.
Ekins, R., Ligand Assays, From Electrophoresis to Miniaturized Microarrays, Clin. Chem. 1998, vol. 44(9), pp. 2015-2030.
Fattinger, C., Koller, H., Schlatter, D., Wehrli, P., 1993, The Difference Interferometer-A High Sensitive Optical Probe for Quantification of Molecular-Surface Concentration, Biosens, Bioelectron 8, pp. 99-107.
Gao, H., et al., Immunosensing With Photo-Immobilized Immunoreagents on Planar Optical Wave Guides. Biosensors and Bioelectronics, 1995, vol. 10, pp. 317-328.
Geissler. M. et al., Microcontact Printing Chemical Patterns With Flat Stamps, J. Am. Chem. Soc., 2000, vol. 122, pp. 6303-6304.

Gruska, B. et al., Fast and Reliable Thickness and Refractive Index Measurement of Antireflection Coatings on Solar-Silicon by Ellipsometry, Sentech Instruments GmbH, CarlOScheele-Str. 16, 12489 Berlin Germany, Sep. 2006.

Grzybowski, B.A., et al., Generation of Micrometer-Sized Patterns for Microanalytical Applications Using a Laser Direct-Write Method and Microcontact Printing, Anal. Chem., 1998, vol. 70, pp. 4645-4652.

Hagman, M., Doing Immunology On A Chip, Science. 2000, vol. 290, pp. 82-83.

He, B. and F.E. Regnier, Fabrication of Nanocolumns for Liquid Chromatography, Anal. Chem., 1998, vol. 70, pp. 3790-3797.

Hecht, E., Optics, 1987, Addison-Wesely Publishing Co., Inc., Menlo Park, CA, pp. 281-286.

Hu, J. et al., Using Soft Lithography to Fabricate GaAs/AlGaAs Heterostructure Field Effect Transistors. Appl. Phys. Lett., 1997 vol. 71, pp. 2020-2022.

Ing R.K. and Monchalin, LP., Broadband Optical Detection of Ultrasound by Two-Wave Mixing in a Photorefractive Crystal, Appl. Phys. Lett. 59, 3233-5 (1991).

Jenison, R., Yan, S. Haeberli, A. Polisky, B., 2001, Interference-Based Detection of Nucleic Acid Targets on Optically Coated Silicon. Nat. Biotechnol. 19, pp. 62-65.

Jenison, Robert et al. Silicon-based Biosensors for Rapid Detection of Protein or Nucleic Acid Targets, Clinical Chemistry, 47:10, 2001 pp. 1894-1990.

Jones, R. et al., Adaptive Femtosecond Optical Pulse Combining, American Institute of Physics, pp. 3692-3694, 2000.

Kapur, Ravi et al. Streamlining the Drug Discovery Process by Integrating Miniaturization High Throughput Screening, High Content Screening, and Automation on the CeliChip TM System. Biomedical Microdevices, vol. 3, No. 2, 1999, pp. 99-109.

Kricka, L.J., Miniaturization of Analytical Systems. Clin. Chem., 1998, vol. 44(9), pp. 2008-2014.

Kunz, R. E., Miniature Integrated Optical Modules for Chemical and Biochemical Sensing. Sensors and Actuators B, 1997, vol. 38-39, pp. 13-28.

Kwolek, K.M. et al., Photorefractive Asymmetric Fabry-Perot Quantum Wells: Transverse-field Geometry, Appl. Phys. Lett., vol. 67, pp. 736-738, 1995.

La Clair, J. et al., Molecular Screening on a Compact Disc, The Royal Society of Chemistry, Org. Biomol. Chem., vol. 1, pp. 3244-3249, 2003.

Lahiri, I. et al., Photorefractive p-i-n. Diode Quantum Well Spatial Light Modulators, American Institute of Physics, Applied Physics Letters, vol. 67, pp. 1408-1410, 1995.

I. Lahiri, L.J. Pyrak, Nolte, D.D. Nolte, M.R Melloch, Ra. Kruger, G.O. Backer, and M. B. Klein, Laser-Based Ultrasound Detection Using Photrefractive Uantum Wells, Appl. Phys. Lett. 73, pp. 104-143 (1998).

Maisenholder., B., et al. A GaAs/AIGaAs-based Refractometer Platform for Integrated Optical Sensing Applications, Sensors and Actuators S, 1997, vol. 38-39, pp. 324-329.

Martin, B.D., et al., Direct Protein Microarray Fabrication Using a Hydrogel Stamper, Langmuir, 1998, vol. 14, pp. 3971-3975.

Marx, J., DNA Arrays Reveal Cancer In Its Many Forms, Science, 2000, vol. 289, pp. 1670-1672.

Montmorillon, La Biaggio, I Delaye, P, Launay, J.C., and Roosen, A, Eye Safe Large Field of View Homodyne Detection Using a Photorefractive CdTe:V Crystal. Opt. Commun. 29, pp. 293 (1996).

Morhard, F. et al., Immobilization of Antibodies in Micropatterns for Cell Detection by Optical Diffraction, Sensors and Actuators B, 2000, vol. 70, pp. 232-242.

Nolte, D.D., Semi-Insulating Semiconductor Heterostructures: Optoelectronic Properties and Applications, Appl. Phys. vol. 85, pp. 6259-6289, 1999.

Nolte, D. D. et al., Adaptive Beam Combining and Interferomety Using Photorefractive Quantum Wells, J. Opt. Soc. Am. B, vol. 19, No. 2, Feb. 2001, pp. 195-205.

Nolte, D.D. et al., Spinning-Disk Interferometry the BioCD, Optics & Photonics News, pp. 48-53, 2004.

Nolte, D. D., Self-Adaptive Optical Holography in Quantum Wells, pp. 1-6, 2005.

Nolte, D., et al., Photorefractive Quantum Wells, 2005.

Peng, Leilei et al., Adaptive Optical Biocompact Disk for Molecular Recognition, Applied Physics Letters 86, pp. 183902-1-183902-3, 2005.

Pompe, T., et al., Submicron Contact Printing on Silicon Using Stamp Pads, Langmuir, 1999, vol. 15, pp. 2398-2401.

Pouet. S.F., Ing. R.K., Krishnaswanry S. and Royer D. Heterodyne Interferometer With Two-Wave Mixing in Photo refractive Crystals for Ultrasound Detection on Rough Surface, Appl. Phys. Lett. 69. pp. 3782 (1996).

Regnier, F.E., et al. Chromatography and Electrophoresis on Chips: Critical Elements of Future.

I. Rossomakhin and Stepanov, Linear Adaptive Interferometers Via Diffusion Recording In Cubic Photorefractive Crystals, Opt. Commun. 86, pp. 199-204 (1991).

Sanders, G.H.W. and A. Manz, Chip-based Microsystems for Genomic and Proteomic Analysis, Trends in Anal, Chem., 2000, vol. 19(6), pp. 364-378.

Scruby, C.B. and L.E. Drain, Laser Ultrasonics: Techniques and Applications. 1990, Bristol: Adam Hilger., pp. 116-123.

Varma, M.M, et al., Spinning-Disk Self-Referencing Interferometry of Antigen-Antibody Recognition, Optics Letters, vol. 29. pp. 950-952, 2004.

Wang, J., Survey and Summary From DNA Biosensors to Gene Chips. Nucl. Acids Res., 2000 vol. 28 (16), pp. 3011-3016.

See, C.W. et al., Scanning Differential Optical Profilometer for Simultaneous Measurement of Amplitude and Phase Variation, Appl. Phys. Lett, vol. 53, No. 1, pp. 10-12, 1988.

Somekh, Michael et al., Scanning Heterodyne Confocal Differential Phase and Intensity Microscope, Applied Optics, vol. 34, No. 22, pp. 4857-4868, 1995.

Burkhart, et al. UCSD Scientists Develop Novel Way to Screen Molecules Using Conventional CDS an Compact Disk Players; UCSD newsletter; pp. 1-4, 2003.

Xia, Y., et al. Non Photolithographic Methods and Fabrication of Elastomeric Stamps for Use in Microcontact Printing, Langmuir, 1996, Vo. 12, pp. 4033-4038.

Suddendorf Manfred, et al., Single-Probe-Beam Differential Amplitude and PhaseScanning Interferometer, Applied Optics, vol. 36, No. 25, pp. 6202-6210, 1997.

Varma, M.M. et al.: High-Speed Label-Free Multi-Analyte Detection Through MicroInterferometry, Proc. of SPIE, vol. 4966, pp. 58-64. 2003.

Varma, M.M., et al., High Speed Label Free Detection by Spinning-Disk Micro-Interferometry, Biosensors & Bioelectronics, vol. 19, pp. 1371-1376, 2004.

St. John et al., Diffraction-Based Cell Detection Using a Microcontact Printed Antibody Grating, Analytical Chemistry, 1998, vol. 70, No. 6, pp. 1108-1111.

Musundi et al, "Approaching Real-Time Molecular Diagnostics: Single-Pair Fluorescence Resonance Energy Transfer (spFRET) Detection for the Analysis of Low Abundant Point Mutations in K-ras Oncogenes," J Am Chem Soc. Jun. 11, 2003;125(23):6937-45.

Lovgren J, Valtonen-Andre C, Marsal K, et al: Measurement of prostate-specific antigen and human glandular kallikrein 2 in different body fluids. J. Androl. 20:348-355, 1999.

J. Homola, "Present and future of surface plasmon resonance biosensors," Analytical and Bioanalytical Chemistry, vol. 377, pp. 528-539, 2003.

Nolte, David D. (2007), "Molecular Interferometry", http://www.nanohub.org/resources/2832/, Jun. 26, 2007 (67 pages).

Michele Ceccarelli, Giuliano Antoniol: A Deformable Grid-Matching Approach for Microarray Images. IEEE Transactions on Image Processing 15(10): 3178-3188 (2006).

Peter Bajcsy: Gridline: automatic grid alignment DNA microarray scans. IEEE Transactions on Image Processing 13(1): 15-25 (2004).

Luis Rueda, Vidya Vidyadharan: A Hill-Climbing Approach for Automatic Gridding of cDNA Microarray Images. IEEE/ACM Trans. Comput. Biology Bioinform. 3(1): 72-83 (2006).

Nagarajan, R., Intensity-based segmentation of microarrays images. IEEE Trans. Med. Imaging. v22. 882-889 (2003).

Faramarzpour, N., Shirani, S. and Bondy, J., Lossless DNA microarray image compression. IEEE Conf. Signal Systems Comput. v2. 1501-1504 (2003).

Katzer, M., Kummert, F. and Sagerer, G., Methods for automatic microarray image segmentation. IEEE Trans. NanoBiosci. v2 i4. 202-214 (2003).

N. Brandle, H. Bischof, H. Lapp: "*Robust DNA Microarray Image Analysis* "; Machine Vision and Applications, 15 (2003), 1; 11-28.

Nagarajan, R and Peterson, C.A. [2002] Identifying Spots in Microarray Images IEEE Trans. Nanobioscience, 1(2), 78-84.

Konstantinos Blekas, Nikolas P. Galatsanos, Aristidis Likas, Isaac E. Lagaris: Mixture model analysis of DNA microarray images. IEEE Trans. Med. Imaging 24(7): 901-909 (2005).

Jinn Ho, Wen-Liang Hwang, Henry Horn-Shing Lu, and D. T. Lee, 'Gridding Spot Centers of Smoothly Distorted Microarray Images', IEEE Trans. on Image Processing, vol. 15, No. 2, Feb. 2006.

Fabri, R: "Towards non-parametric gidding of Microarray images," Digital Signal Processing, 2002. DSP 2002. 2002 14th International Conference publication, Volume: 2, pp. 623-626.

H. Vikalo, B. Hassibi, and A. Hassibi, "A statistical model for microarrays, optimal estimation algorithms, and limits of performance," IEEE Transactions on Signal Processing, Special Issue on Genomics Signal Processing, vol. 54, No. 6, Jun. 2006, pp. 2444-2455.

Chiao-Ling Shih, Hung-Wen Chiu, "Automatic spot detection of cDNA Microarray images using mathematical morphology methods," Conference on IEEE EMBS Asian-Pacific, Oct. 2003, pp. 70-71.

MacBeath, G. and S.L. Schreiber. 2000. "Printing proteins as microarrays for high-throughput function determination." Science 289:1760-1763.

Guemouri, L., J. Ogier, and J. J. Ramsden, "Optical properties of protein monolayers during assembly." Journal of Chemical Physics 1998. 109:3265-3268.

Ostroff, R., A. Ettinger, H. La, M. Rihanek, L. Zalman, J. Meador III, A. K. Patick, S. Worland, and B. Polisky. 2001. "Rapid multiserotype detection of human rhinoviruses on optically coated silicon surfaces." J. Clin. Virol. 21: 105-117.

H. Ozen and S. Sozen, "PSA Isoforms in prostate cancer detection," *Eur. Urol. Suppl.*, vol. 5, pp. 495-499, 2006.

N. B. Sheller, S. Petrash, M.D. Foster, "Atomic Force Microscopy and X-ray Reflectivity Studies of Albumin Adsorbed onto Self-Assembled Monolayers of Hexadecyltrichlorosilane," *Langmuir*, 14, 4535-4544, 1998.

M. Varma, D. D. Nolte, H. D. Inerowicz, and F. E. Regnier, "Multi-Analyte Array Micro-Diffraction Interferometry," in *Microarrays: Design, Fabrication and Reading* vol. 4626, B. J. B. e. al., Ed.: SPIE, 2002, pp. 69-77.

D. D. Nolte and M. R. Melloch, "Photorefractive Quantum Wells and Thin Films," in *Photorefractive Effects and Materials*, D. D. Nolte, Ed. Dordrecht: Kluwer Academic Publishers, pp. 373-451, 1995.

D. S. Gerber, R. Droopad, and G. N. Maracas, "A GaAs/AlGaAs Asymmetric FabryPerot Reflection Modulator with very High Contrast Ratio," *IEEE Phot. Tech Lett.*, vol. 5, pp. 55-58, 1993.

M. Whitehead and G. Parry, "High-contrast reflection modulation at normal incidence in asymmetric multiple quantum well Fabry-Perot structure," *Electron. Lett.*, vol. 25, pp. 566-568, 1989.

B. J. Luff, J. S. Wilkinson, J. Piehler, U. Hollenbach, J. Ingenhoff, and N. Fabricius, "Integrated optical Mach-Zehnder biosensor," *Journal of Lightwave Technology*, vol. 16, pp. 583-592, 1998.

B. Drapp, J. Piehler, A. Brecht, G. Gauglitz, B. J. Luff, J. S. Wilkinson, and J. Ingenhoff, "Integrated optical Mach-Zehnder interferometers as simazine immunoprobes,"*Sensors and Actuators B-Chemical*, vol. 39, pp. 277-282, 1997.

L. U. Kempen and R. E. Kunz, "Replicated Mach-Zehnder interferometers with focusing grating couplers for sensing applications," *Sensors and Actuators B-Chemical*, vol. 39, pp. 295-299, 1997.

V. S.-Y. Lin, K. Motesharei, K.-P. S. Dancil, M. Sailor, and M. R. Ghadiri, "A porous silicon-based optical interferometric biosensor," *Science*, vol. 278, pp. 840-843, 1997.

Y. C. Cao, R. Jin, and C. A. Mirkin, "Nanoparticles with Raman Spectroscopic Fingerprints for DNA and RNA Detection," *Science*, vol. 297, pp. 1536-1540, 2002.

T. A. Taton, C. A. Mirkin, and R. L. Letsinger, "Scanometric DNA Array Detection with Nanoparticle Probes," *Science*, vol. 289, pp. 1757-1760, 2000.

C. Gurtner, E. Tu, N. Jamshidi, R. W. Haigis, T. J. Onofrey, C. F. Edman, R. Sosnowski, B. Wallace, and M. J. Beller, "Microelectronic array devices and techniques for electric field enhanced DNA hybridization in low-conductance buffers," *Electrophoresis*, vol. 23, pp. 1543-50, 2002.

Y. Joon Mo, J. Bell, H. Ping, M. Tirado, D. Thomas, A. H. Forster, R. W. Haigis, P. D. Swanson, R. B. Wallace, B. Martinsons, and M. Krihak, "An integrated, stacked microlaboratory for biological agent detection with DNA and immunoassays," *Biosensors & Bioelectronics*, vol. 17, pp. 605-18, 2002.

J. Heller, "An active microelectronics device for multiplex DNA analysis," *IEEE Engineering in Medicine & Biology Magazine*, vol. 15, pp. 100-4, 1996.

D. D. Nolte and K. M. Kwolek, "Diffraction from a Short-Cavity Fabry-Perot: Applications to Photorefractive Quantum Wells," *Opt. Commun.*, vol. 115, pp. 606-616, 1995.

R.-H. Yan, R. J. Simes, and L. A. Coldren, "Analysis and design of surface-normal Fabry-Perot electrooptic modulators," *IEEE Quant. Electron.*, vol. 25, pp. 2272-2280, 1989.

J. F. Heffernan, M. H. Moloney, J. Hegarty, J. S. Roberts, and M. Whitehead, "All optical high contrast absorptive modulation in an asymmetric Fabry-Perot etalon," *Appl. Phys. Lett.*, vol. 58, pp. 2877-2879, 1991.

A. Larsson and J. Maserjian, "Optically addressed asymmetric Fabry-Perot modulator," *Appl. Phys. Lett.*, vol. 59, pp. 3099-3101, 1991.

K. M. Kwolek, M. R. Melloch, and D. D. Nolte, "Dynamic holography in a reflection/transmission photorefractive quantum-well asymmetric Fabry-Perot," *Appl. Phys. Lett.*, vol. 65, pp. 385-387, 1994.

D. D. Nolte, "Dynamic Holographic Phase Gratings in Multiple Quantum Well Asymmetric Reflection Fabry-Perot Modulators," *Opt. Lett.*, vol. 19, pp. 819-821, 1994.

P. Balk, Y.-J. Ko, and G. J. Bubley, "Biology of Prostate-specific antigen," J. Clin. Onc., vol. 21, pp. 383-391, 2003.

Wang, M.C., Papsidero, L.D., Kuriyama, M., Valenzuela, G.P. and Chu, T.M. 1981. Prostate antigen: A new potential marker for prostatic cancer. *The Prostate* 2: 89-96.

T. Cass and F. S. Ligler, "Immobilized Biomolecules in Analysis: A Practical Approach," Oxford: Oxford, 1998.

R. Guersen, I. Lahiri, M. R. Melloch, J. M. Woodall and D. D Nolte, Transient Enhanced Intermixing of Arsenic-Rich Nonstoichiometric AlAs/GaAs Quantum Wells, Phys. Rev. B60,10926-10934 (1999).

D. Crouse, D. D. Nolte, J. C. P. Chang, and M. R. Melloch, "Optical absorption by Ag precipitates in AlGaAs," *J. Appl. Phys.*, vol. 81, pp. 7981-7987, 1997.

G. A. Sefler, E. Oh, R. S. Rana, I. Miotkowski, A. K. Ramdas, and D. D. Nolte, "Faraday Photorefractive Effect in a Diluted Magnetic Semiconductor," *Opt. Lett.*, vol. 17, pp. 1420-1422, 1992.

J. M. McKenna, D. D. Nolte, W. Walukiewicz, and P. Becla, "Persistent holographic absorption gratings in AlSb:Se,"*Appl. Phys. Lett.*, vol. 68, pp. 735-737, 1996.

R. S. Rana, E. Oh, K. Chua, A. K. Ramdas, and D. D. Nolte, "Voigtphotorefractive two-wave mixing in CdMnTe," *J. Lumin.*, vol. 60&61, pp. 56-59, 1994.

L. Peng, P. Yu, D. D. Nolte, and M. R. Melloch, "High-speed adaptive interferometer for optical coherence-domain reflectometry through turbid media," Opt. Lett. 28, 396-398 (2003).

R. M. Brubaker, Y. Ding, D. D. Nolte, M. R. Melloch, and A. M. Weiner, "Bandwidth-Limited Diffraction of Femtosecond Pulses from Photorefractive Quantum Wells," *IEEE J. Quant. Electron.*, vol. 33, pp. 2150-2158, 1997.

Y. Ding, D. D. Nolte, M. R. Melloch, and A. M. Weiner, "Real-time edge enhancement of femtosecond time-domain images by use of photorefractive quantum wells," *Opt. Lett.*, vol. 22, pp. 1101-1103, 1997.

Y. Ding, D. D. Nolte, M. R. Melloch, and A. M. Weiner, "Time-domain image processing using dynamic holography," *IEEE J. Sel. Top. Quant. Elect.*, vol. 4, pp. 332-341, 1998.

M. Dinu, D. D. Nolte, and M. R. Melloch, "Electroabsorption spectroscopy of effectivemass AlGaAs/GaAs Fibonacci superlattices," *Phys. Rev. B*, vol. 56, pp. 1987-1995, 1997.

M. Dinu, K. Nakagawa, M. R. Melloch, A. M. Weiner, and D. D. Nolte, "Broadband LowDispersion Diffraction of Femtosecond Pulses from Photorefractive Quantum Wells," *J. Opt. Soc. Am. B*, vol. 17, pp. 1313-1319, 2000.

Y. Ding, D. D. Nolte, Z. Zheng, A. Kanan, A. M. Weiner, and G. A. Brost, "Bandwdith Study of Volume Holography in Photorefrative InP:Fe at 1.5 microns for Frequency Domain Femtosecond Pulse Processing," *J. Opt. Soc. B*, vol. 15, pp. 2763-68, 1998.

Y. Ding, I. Lahiri, D. D. Nolte, G. J. Dunning, and D. M. Pepper, "Electric Field Correlation of Femtosecond Pulses Using a Photo-Electromotive Force Detector,"*J. Opt. Soc. Am. B*, vol. 15, pp. 2013-17, 1998.

R. Jones, N. P. Barry, S. C. W. Hyde, P. M. W. French, K. M. Kwolek, D. D. Nolte, and M. R. Melloch, "Direct-to-Video holographic readout in quantum wells for 3-D imaging through turbid media," *Opt. Lett.*, vol. 23, pp. 103-105, 1998.

R. Jones, M. Tziraki, P. M. W. French, K. M. Kwolek, D. D. Nolte, and M. R. Melloch, "Direct-tovideo holographic 3-D imaging using photorefractive multiple quantum well devices," *Optics Express*, vol. 2, pp. 439-448, 1998.

M. Tziraki, R. Jones, P. M. W. French, M. R. Melloch, and D. D. Nolte, "Photorefractive Holography for Imaging through turbid media using low coherence light," *Appl. Phys. B*, vol. 70, pp. 151-154, 1999.

M. Tziraki, R. Jones, P. French, D. Nolte, and M. Melloch, "Short-coherence photorefractive holography in multiple-quantum-well devices using light-emitting diodes," *Appl. Phys. Lett.*, vol. 75, pp. 363-5, 1999.

I. Lahiri, D. D. Nolte, M. R. Melloch, and M. B. Klein, "Oscillatory mode coupling and electrically strobed gratings in photorefractive quantum-well diodes," *Optics Lett.*, vol. 23, pp. 49-51, 1998.

I. Lahiri, L. J. Pyrak-Nolte, D. D. Nolte, and M. R. Melloch, "Transient Dynamics During Two-Wave Mixing in Photorefractive Quantum Well Diodes using Moving Gratings," *Opt. Express*, vol. 2, pp. 432-438, 1998.

C.-C. Wang, R. A. Linke, D. D. Nolte, M. R. Melloch, and S. Trivedi, "Enhanced detection bandwidth for optical doppler frequency measurements using moving space charge field effects in GaAs multiple quantum wells," *Appl. Phys. Lett.*, vol. 70, pp. 2034-2036, 1997.

C. Wang, R. A. Linke, D. D. Nolte, M. R. Melloch, and S. Trivedi, "Signal strength enhancement and bandwidth tuning in moving space charge field photodetectors using alternating bias field," *Appl. Phys. Lett.*, vol. 72, pp. 100-102, 1998.

M. Pepper, G. J. Dunning, M. P. Chiao, T. R. O'Meara, P. V. Mitchell, I. Lahiri, and D. D. Nolte, "Characterization of the photo-EMF response for laser-based ultrasonic sensing under simulated industrial conditions," *Rev. Prog. Quant. Nondestruct. Eval.*, vol. 17, pp. 627-634, 1998.

D. D. Nolte, Mesoscopic Pointlike Defects in Semiconductors: Deep-level Energies, Phys. Rev. B 58, 7994-8001 (1998).

M. Dinu, I. Miotkowski and D. D. Nolte, Magnetic Quenching of Time-Reversed Light in Photorefractive Diluted Magnetic Semiconductors, Phys. Rev. B 58, 10435 (1998).

S. Balasubramanian, S. W. Mansour, M. R. Melloch and D. D. Nolte, Vacancy diffusion Kinetics in arsenic-rich nonstoichiometric AlAs/GaAs heterostructures, Phys. Rev. B 63, 033305-1—033305-3 (2000).

David D. Nolte, Manoj M. Varma, Leilei Peng, Halina D. Inerowicz, Fred E. Regnier, Spinning-disk laser interferometers for immunoassays and proteomics: the BioCD in Proc. SPIE vol. 5328, Microarrays and Combinatorial Techniques: Design, Fabrication, and Analysis II; Dan V. Nicolau, Ramesh Raghavachari; Eds., p. 41-48 (2004).

Manoj M. Varma, Halina D. Inerowicz, Fred E. Regnier, David D. Nolte, Real-time spinning-disk interferometric immunoassays, in Proc. SPIE vol. 5328, Microarrays and Combinatorial Techniques: Design, Fabrication, and Analysis II; Dan V. Nicolau, Ramesh Raghavachari; Eds., p. 62-68.

T. Jensen, L Kelly, A. Lazarides, and G. C. Schatz, "Electrodynamics of noble metal nanoparticles and nanoparticle clusters,"*Journal of Cluster Science*, vol. 10, pp. 295-317, 1999.

H. Kuwata, H. Tamaru, K. Esumi, and K. Miyano, "Resonant light scattering from metal nanoparticles: Practical analysis beyond Rayleigh approximation," *Applied Physics Letters*, vol. 83, pp. 4625-4627, 2003.

M.J. Jory, P. S. Cann, J. R. Sambles, and E. A. Perkins, "Surface-plasmon-enhanced light scattering from microscopic spheres," *Applied Physics Letters*, vol. 83, pp. 3006-3008, 2003.

K.L. Kelly, E. Coronado, L. L. Zhao, and G. C. Schatz, "The optical properties of metal nanoparticles: the influence of size, shape, and dielectric environment," *Journal of Physical Chemistry B*, vol. 107, pp. 668-677, 2003.

P. Chakraborty, "Metal nanoclusters in glasses as non-linear photonic materials,"*Journal of Materials Science*, vol. 33, pp. 2235-2249, 1998.

S.J. Oldenburg, S. L. Westcott, R. D. Averitt, and N. J. Halas, "Surface enhanced Raman scattering in the near infrared using metal nanoshell substrates,"*Journal of Chemical Physics*, vol. 111, pp. 4729-4735, 1999.

P. Mulvaney, "Surface plasmon spectroscopy of nanosized metal particles," *Langmuir*, vol. 12, pp. 788-800, 1996.

H.F. Ghaemi, T. Thio, D. E. Grupp, T. W. Ebbesen, and H. J. Lezec, "Surface plasmons enhance optical transmission through subwavelength holes," *Physical Review B*, vol. 58, pp. 6779-6782, 1998.

T.W. Ebbesen, H. J. Lezec, H. F. Ghaemi, T. Thio, and P. A. Wolff, "Extraordinary optical transmission through sub-wavelength hole arrays," *Nature*, vol. 391, pp. 667-669, 1998.

D.A. Genov, A. K. Sarychev, V. M. Shalaev, and A. Wei, "Resonant field enhancements from metal nanoparticle arrays," *Nano Letters*, vol. 4, pp. 153-158, 2004.

V. Koubova, E. Brynda, L. Karasova, J. Skvor, J. Homola, J. Dostalek, P. Tobiska, and J. Rosicky, "Detection of food borne pathogens using surface plasmon resonance biosensors," Sensors and Actuators B-Chemical, vol. 74, pp. 100-105, 2001.

M. Minunni and M. Mascini, "Detection of Pesticide in Drinking-Water Using Real-Time Biospecific Interaction Analysis (Bia),"*Analytical Letters*, vol. 26, pp. 1441-1460, 1993.

C. Mouvet, R. D. Harris, C. Maciag, B. J. Luff, J. S. Wilkinson, J. Piehler, A. Brecht, G. Gauglitz, R. Abuknesha, and G. Ismail, "Determination of simazine in water samples by waveguide surface plasmon resonance," Analytica Chimica Acta, vol. 338, pp. 109-117, 1997.

A. Rasooly, "Surface plasmon resonance analysis of staphylococcal enterotoxin B in food," *Journal of Food Protection*, vol. 64, pp. 37-43, 2001.

G. Sakai, K. Ogata, T. Uda, N. Miura, and N. Yamazoe, "A surface plasmon resonancebased immunosensor for highly sensitive detection of morphine," Sensors and Actuators B-Chemical, vol. 49, pp. 5-12, 1998.

G. Sakai, S. Nakata, T. Uda, N. Miura, and N. Yamazoe, "Highly selective and sensitive SPR immunosensor for detection of methamphetamine," Electrochimica Acta, vol. 44, pp. 3849-3854, 1999.

E. Kretschmann and H. Raether, "Radiative Decay of Non Radiative Surface Plasmons Excited by Light," *Zeitschrift Fur Naturforschung Part a-Astrophysik Physik Und Physikalische Chemie*, vol. A 23, pp. 2135-2136, 1968.

A. Otto, "Excitation of Nonradiative Surface Plasma Waves in Silver by Method of Frustrated Total Reflection," *Zeitschrift Fur Physik*, vol. 216, pp. 398-410, 1968.

J. Homola, S. S. Yee, and G. Gauglitz, "Surface plasmon resonance sensors: review," Sensors and Actuators B-Chemical, vol. 54, pp. 3-15, 1999.

M. Malmqvist, "BIACORE: an affinity biosensor system for characterization of biomolecular interactions," *Biochemical Society Transactions*, vol. 27, 1999.

M. Fivash, E. M. Towler, and R. J. Fisher, "BIAcore for macromolecular interaction," Current Opinion in Biotechnology, vol. 9, pp. 97-101, 1998.

L. D. Roden and D. G. Myszka, "Global analysis of a macromolecular interaction measured on BIAcore," Biochemical and Biophysical Research Communications, vol. 225, pp. 1073-1077, 1996.

C. F. R. Mateus, M. C. Y. Huang, B. T. Cunningham, and C. J. Chang-HASNAIN, "Compact label-free biosensor using VCSEL-based measurement system," Ieee Photonics Technology Letters, vol. 16, pp. 1712-1714, 2004.

P. Y. Li, L. Bo, J. Gerstenmaier, and B. T. Cunningham, "A new method for label-free imaging of biomolecular interactions," Sensors and Actuators B-Chemical, vol. 99, pp. 6-13, 2004.

G. Walter, K. Bussow, A. Lueking, and J. Glokler, "High-throughput protein arrays: prospects for molecular diagnostics," Trends in Molecular Medicine, vol. 8, pp. 250-253, 2002.

J.B. Pendry, L. Martin-Moreno, and F. J. Garcia-Vidal, "Mimicking surface plasmons with structured surfaces," Science, vol. 305, pp. 847-848, 2004.

A.G. Brolo, R. Gordon, B. Leathem, and K. L. Kavanagh, "Surface plasmon sensor based on the enhanced light transmission through arrays of nanoholes in gold films," Langmuir, vol. 20, pp. 4813-4815, 2004.

J. A. Coy, D. D. Nolte, G. J. Dunning, D. M. Pepper, B. Pouet, G. D. Bacher, and M. B. Klein, "Asymmetric Interdigitated MSM Contacts for Improved Adaptive Photo-EMF Detectors," J. Opt. Soc. Am. B, vol. 17, pp. 697-704, 1999.

J. Coy, F. Stedt, I. Lahiri, M. Melloch, and D. Nolte, "Exciton electroabsorption moments and sum rules," Opt. Commun., vol. 176, pp. 17-29, 2000.

R. S. Rana, E. Oh, K. Chua, A. K. Ramdas, and D. D. Nolte, "Magneto-photorefractive effects in a diluted magnetic semiconductor," Phys. Rev. B, vol. 49, pp. 7941-7951, 1994.

D. D. Nolte, I. Lahiri, J. Mckenna, F. R. Steldt, J. C. P. Chang, M. R. Melloch, and J. M. Woodall, "%tinier excitons in a Coulomb Cage," presented at 23rd Int. Conf. Phys. Semicond., Vancouver, Canada, 1994.

D. D. Nolte, J. A. Coy, G. J. Dunning, D. M. Pepper, M. P. Chiao, G. D. Bacher, and M. B. Klein, "Enhanced responsivity of non-steady-state photoinduced electromotive force sensors using asymmetric interdigitated contacts," Opt. Lett., vol. 24, pp. 342-344, 1999.

D. M. Pepper, G. J. Dunning, D. D. Nolte, J. Coy, M. B. Klein, G. D. Backer, and B. Pouet, "Enhanced Responsivity of Photo-Induced-emf Laser Ultrasound Sensors Using Asymmetric Interdigitated Contacts," in Review of Progress in Quantitative Nondestructive Evaluation, vol. 19, D. O. Thompson and D. E. Chimenti, Eds. New York: American Institute of Physics Press, 2000, pp. 2013-2020.

Technology paper entitled "Grating-Coupled Surface Plasmon Resonance (GCSPR)" —printed from HTS Biosystems Technologies website (www.htsbiosystems.com/technology/gcspr.htm) on May 2, 2005.

B. Cunningham, P. Li, and J. Pepper, "Colorimetric resonant reflection as a direct biochemical assay technique," Sensors and Actuators B, vol. 81, pp. 316-328, 2002.

X. Wang, M. Zhao, and D. D. Nolte, "Common-path interferometric detection of protein monolayer on the BioCD," Appl. Opt 46, 7836-7849 (2007).

X. Wang and D. Nolte, " The Bragg Side-Band BioCD," in Conference on Lasers and Electro-Optics/Quantum Electronics and Laser Science Conference and Photonic Applications Systems Technologies, OSA Technical Digest (CD) (Optical Society of America, 2007), 2 pages.

Polizzi, M.A., Plocinik, R.M., and Simpson, G.J., "Ellipsometric Approach for the Real-Time Detection of Label-Free Protein Adsorption by Second Harmonic Generation," J. Am. Chem. Soc., 126, 15, 5001-5007, 2004.

Plocinik, R. M.; Simpson, G. J., Polarization characterization in surface second harmonic generation by nonlinear optical null ellipsometry. Analytica Chimica Acta 2003, 496, (1-2), 133-142.

P. B. Luppa, L J. Sokoll, and D. W. Chan, "Immunosensors—principles and applications to clinical chemistry," *Clinica Chimica Acta*, vol. 314, pp. 1-26, 2001.

C. L. Tucker, J. F. Gera, and P. Uetz, "Towards an understanding of complex protein networks," *Trends in Cell Biology*, vol. 11, pp. 102-106, 2001.

P. Uetz and R. L. Finley, "From protein networks to biological systems," *Febs Letters*, vol. 579, pp. 1821-1827, 2005.

G. Gauglitz, "Direct optical sensors: principles and selected applications," Analytical And Bioanalytical Chemistry, vol. 381, pp. 141-155, 2005.

M. Zhao, D. D. Nolte, W. R. Cho, F. Regnier, M. Varma, G. Lawrence, and J. Pasqua, "High-speed interferometric detection of label-free immunoassays on the biological compact disc," *I Clin. Chem.*, vol. 52, pp. 2135-2140, 2006.

David D. Nolte and Ming Zhao, "Scaling mass sensitivity of the BioCD at 0.25 pg/mm," Proc. SPIE hit. Soc. Opt. Eng. 6380, 63800J (2006), D01:10.1117/12.686307 (6 pages).

Nolte, D.D., Self-Adaptive Optical Holography in Quantum Wells, Pro. Of SPIE, vol. 3729, pp. 237-243 (1999).

Delaye, P., et al., Detection of Ultraonic Motion of a Scattering Surface by Two Wave mixing In a Photorefractive GaAs Crystal, Appl. Phys. Litt. 65, 932-4 (1994).

* cited by examiner

US 8,298,831 B2

DIFFERENTIALLY ENCODED BIOLOGICAL ANALYZER PLANAR ARRAY APPARATUS AND METHODS

RELATED APPLICATIONS

This application is a divisional of U.S. patent application Ser. No. 11/345,566, filed Feb. 1, 2006 now abandoned, the complete disclosure of which is hereby expressly incorporated herein by this reference. This application also claims the benefit of U.S. Provisional Patent Application Ser. No. 60/648,724 filed Feb. 1, 2005, the complete disclosure of which is hereby expressly incorporated herein by this reference.

GOVERNMENTAL SUPPORT INFORMATION

This invention was made with government support under grant reference number NSF ECS-0200424 awarded by the National Science Foundation. The Government has certain rights in the invention.

TECHNICAL FIELD

The present invention generally relates to apparatus, methods and systems for detecting the presence of one or more target analytes or specific biological materials in a sample, and more particularly to a laser compact disc system for detecting the presence of biological materials and/or analyte molecules bound to target receptors on a disc by sensing changes in the optical characteristics of a probe beam reflected, transmitted, or diffracted by the disc caused by the materials and/or analytes.

BACKGROUND OF THE INVENTION

In many chemical, biological, medical, and diagnostic applications, it is desirable to detect the presence of specific molecular structures in a sample. Many molecular structures such as cells, viruses, bacteria, toxins, peptides, DNA fragments, pathogens, and antibodies are recognized by particular receptors. Biochemical technologies including gene chips, immunological chips, and DNA arrays for detecting gene expression patterns in cancer cells, exploit the interaction between these molecular structures and the receptors. [For examples see the descriptions in the following articles: Sanders, G. H. W. and A. Manz, *Chip-based Microsystems for genomic and proteomic analysis*. Trends in Anal. Chem., 2000, Vol. 19(6), p. 364-378. Wang, J., *From DNA biosensors to gene chips*. Nucl. Acids Res., 2000, Vol. 28(16), p. 3011-3016; Hagman, M., *Doing immunology on a chip*. Science, 2000, Vol. 290, p. 82-83; Marx, J., *DNA Arrays reveal cancer in its many forms*. Science, 2000, Vol. 289, p. 1670-1672]. These technologies generally employ a stationary chip prepared to include the desired receptors (those which interact with the target analyte or molecular structure under test). Since the receptor areas can be quite small, chips may be produced which test for a plurality of analytes. Ideally, many thousand binding receptors are provided to provide a complete assay. When the receptors are exposed to a biological sample, only a few may bind a specific protein or pathogen. Ideally, these receptor sites are identified in as short a time as possible.

One such technology for screening for a plurality of molecular structures is the so-called immunological compact disk, which simply includes an antibody microarray. [For examples see the descriptions in the following articles: Ekins, R., F. Chu, and E. Biggart, *Development of microspot multianalyte ratiometric immunoassay using dual flourescent-labelled antibodies*. Anal. Chim. Acta, 1989, Vol. 227, p. 73-96; Ekins, R. and F. W. Chu, *Multianalyte microspot immunoassay—Microanalytical "compact Disk" of the future*. Clin. Chem., 1991, Vol. 37(11), p. 1955-1967; Ekins, R., *Ligand assays: from electrophoresis to miniaturized microarrays*. Clin. Chem., 1998, Vol. 44(9), p. 2015-2030]. Conventional fluorescence detection is employed to sense the presence in the microarray of the molecular structures under test. Other approaches to immunological assays employ traditional Mach-Zender interferometers that include waveguides and grating couplers. [For examples see the descriptions in the following articles: Gao, H., et al., *Immunosensing with photo-immobilized immunoreagents on planar optical wave guides*. Biosensors and Bioelectronics, 1995, Vol. 10, p. 317-328; Maisenholder, B., et al., *A GaAs/AlGaAs-based refractometer platform for integrated optical sensing applications*. Sensors and Actuators B, 1997, Vol. 38-39, p. 324-329; Kunz, R. E., *Miniature integrated optical modules for chemical and biochemical sensing*. Sensors and Actuators B, 1997, Vol. 38-39, p. 13-28; Dübendorfer, J. and R. E. Kunz, *Reference pads for miniature integrated optical sensors*. Sensors and Actuators B, 1997 Vol. 38-39, p. 116-121; Brecht, A. and G. Gauglitz, *recent developments in optical transducers for chemical or biochemical applications*. Sensors and Actuators B, 1997, Vol. 38-39, p. 1-7]. Interferometric optical biosensors have the intrinsic advantage of interferometric sensitivity, but are often characterized by large surface areas per element, long interaction lengths, or complicated resonance structures. They also can be susceptible to phase drift from thermal and mechanical effects. Current practice is to perform long time integrations (as in fluorescence detection) to achieve a significant signal. However, the long integration times place the measurement firmly in the range of 1/f noise (frequency=1/τ, where τ is the measurement time). Likewise, SPR measurement approaches (for example systems from Biacore) or resonant mirror approaches (for example systems from SRU Biosystems) are angle resolved or wavelength resolved, requiring detailed measurements that take long integration times.

While the abovementioned techniques have proven useful for producing and reading assay information within the chemical, biological, medical and diagnostic application industries, developing improved fabrication and reading techniques for planar arrays with significant improvement in performance over existing planar array technology is desirable.

SUMMARY OF THE INVENTION

One embodiment according to the present invention includes a method of probing a plurality of analyzer molecules distributed about a detection platform. The method includes contacting a test sample to the plurality of analyzer molecules, scanning the plurality of analyzer molecules at a rate relating to a carrier frequency signal, and detecting the presence or absence of a biological molecule based at least in part upon the presence or absence of a signal substantially at a sideband of the carrier frequency signal.

Another embodiment according to the present invention includes a molecule detection platform including a substrate and a plurality of targets positioned about the substrate. Specific analyzer molecules adapted to bind a specific analyte are immobilized about a first set of the targets. Nonspecific analyzer molecules are immobilized about a second set of the targets. The targets positioned about the substrate along at least a segment of a scanning pathway alternate between at least one of the first set and at least one of the second set.

A further embodiment according to the present invention includes a method including providing a substrate for supporting biological analyzer molecules. The substrate includes at least one scanning pathway. The scanning pathway including a plurality of scanning targets. The method further includes distributing specific biological analyzer molecules adapted to detect a specific target analyte about a first set of the targets which alternate in groups of at least one with a second set of the targets. The second set of the targets does not include the specific biological analyzer molecules.

Additional embodiments, aspects, and advantages of the present invention will be apparent from the following description.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
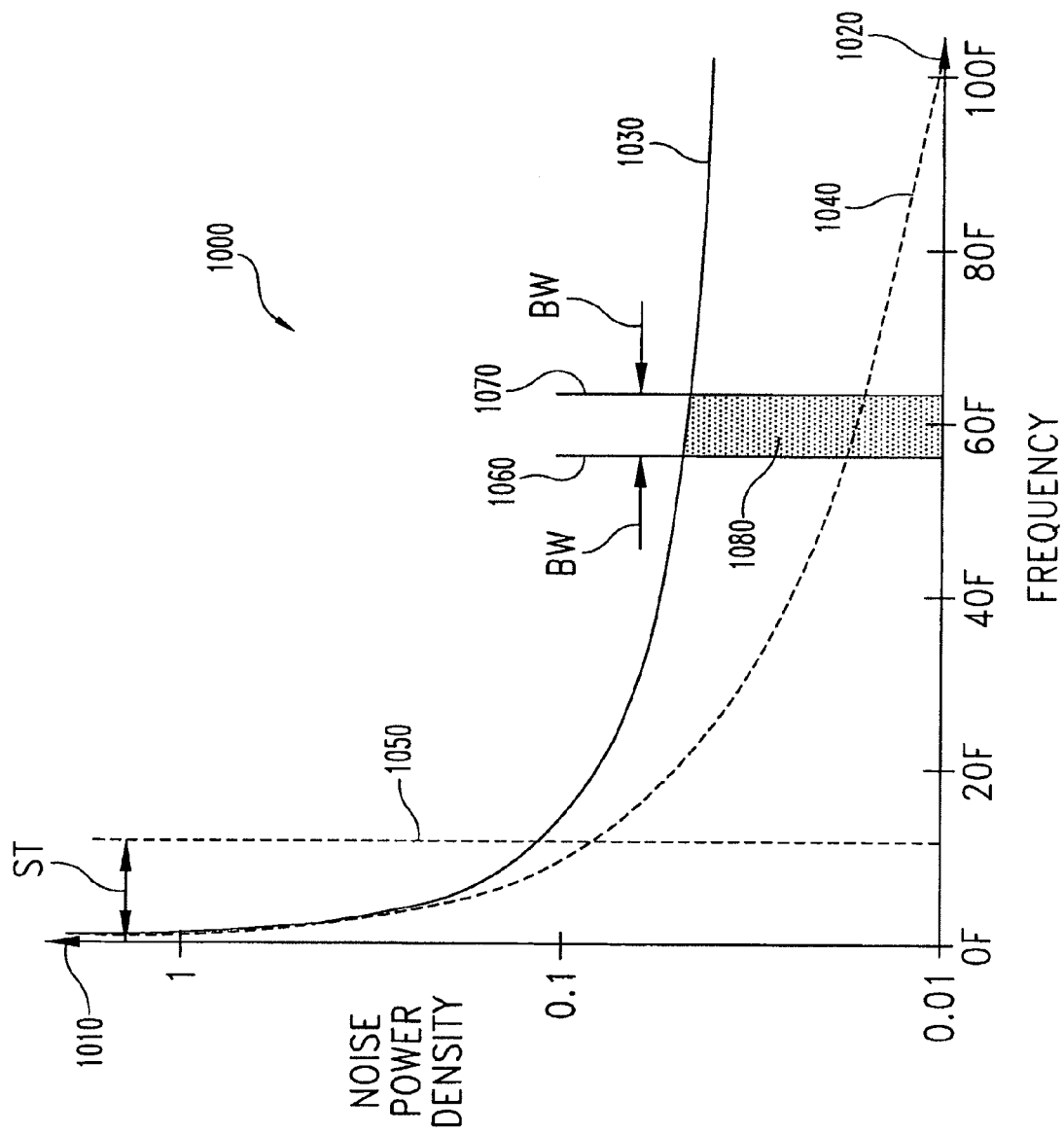
FIG. 1 shows a graph of noise power density versus frequency according to an embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

With reference to FIG. 1 there is shown graph 1000 with frequency increasing along its x axis as indicated by x axis arrow 1020 and noise power density increasing along its y axis as indicated by its y axis arrow 1010. Frequency can be either temporal frequency (Hz) or spatial frequency (1/cm). Graph 1000 illustrates noise power density versus frequency in the absence of a carrier frequency. Curve 1030 illustrates the noise power density of total noise as it varies with frequency. Curve 1040 illustrates the noise power density of 1/f noise as it varies with frequency. A bandwidth between frequencies 1060 and 1070 is indicated by arrows BW. The total noise for this bandwidth is given by the area under curve 1030 labeled 1080 which represents detected noise power for a measurement taken at bandwidth BW. The frequency range where only static is detectable is illustrated by arrows ST. The frequency value of the 1/f noise knee is illustrated by line 1050 and represents the frequency above which a signal may be detected over noise.

Figure 2:
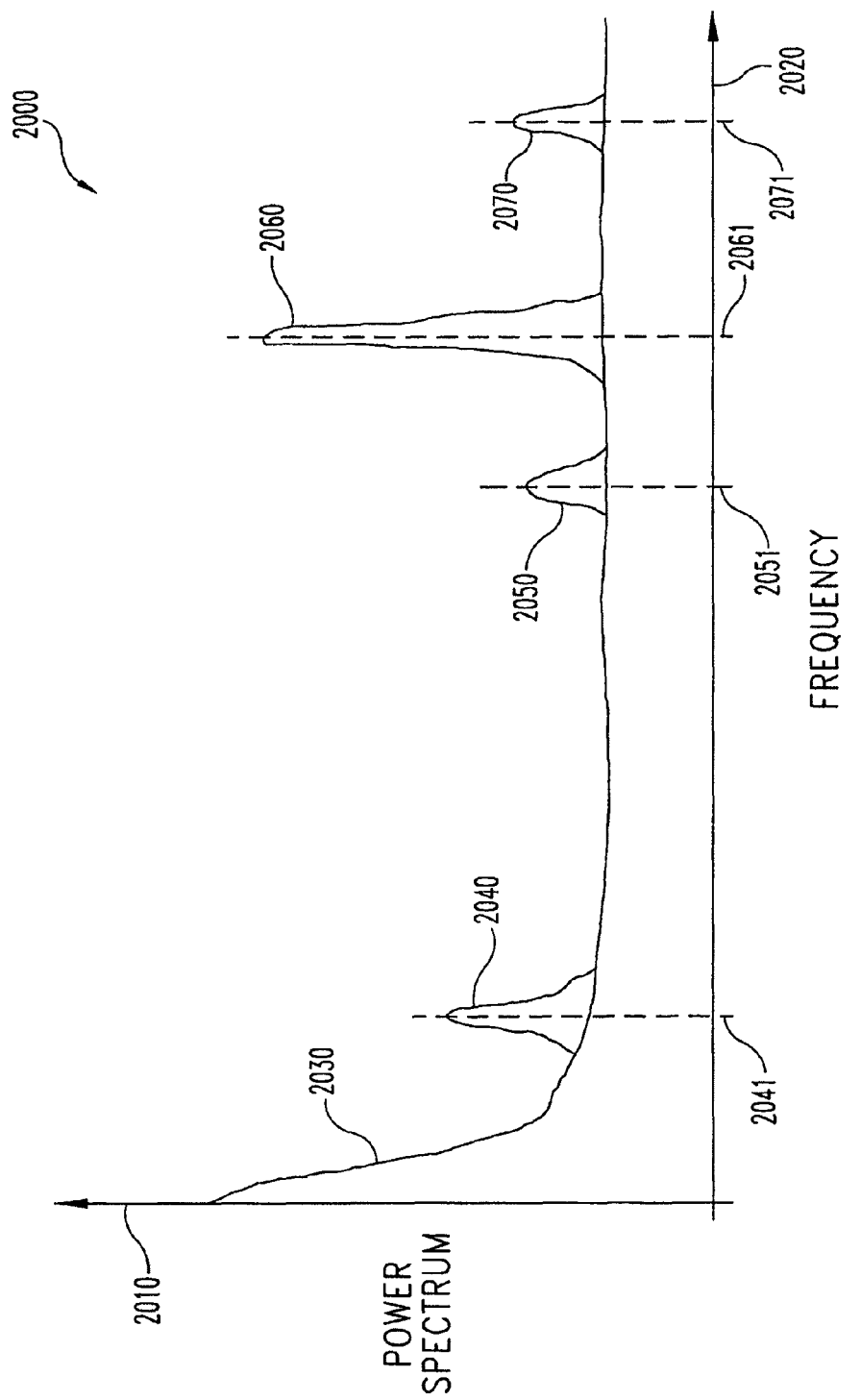
FIG. 2 shows a graph of power spectrum versus frequency according to an embodiment of the present invention.

With reference to FIG. 2 there is shown graph 2000 with frequency increasing along its x axis as indicated by x axis arrow 2020 and power spectrum increasing along its y axis as indicated by y axis arrow 2010. The power level of 1/f noise is illustrated by curve 2030. A DC sideband signal 2040 having DC sideband center frequency 2041, a carrier signal 2060 having carrier center frequency 2061, and carrier sidebands 2050 and 2070 having carrier sideband center frequencies 2051 and 2071, respectively, are also shown.

Graph 2000 illustrates one example of frequency domain detection of the molecular, cellular, or particulate content of a liquid or air sample in which an analyte binds on or in a support material to produce a periodic, quasi-periodic or harmonic modulation of phase or amplitude of an electromagnetic wave that probes the support material. The periodic or quasi-periodic modulation can be in time or space, leading to a time-domain carrier frequency or a space-domain carrier frequency, by relative motion of the probe beam and support. The presence of the bound analyte appears as a modulation sideband of the carrier frequency. As shown in graph 2000, carrier sideband signals 2050 and 2070 indicate the presence of one or more target analytes bound to analyzer molecules distributed about a support material which is probed with an electromagnetic wave in a detection system. The detection system preferably includes a photodetector, or another detector responsive to electromagnetic waves, that outputs a current as described below by Equation 1:

$$i(t) = \frac{1}{2}(1 + \cos\omega_c t)(1 + A\cos\omega_m t)$$

Equation 1 has a harmonic decomposition described by Equation 2:

$$i(t) = \frac{1}{2} + \frac{1}{2}\cos\omega_c t + \frac{A}{2}\cos\omega_m t + \frac{A}{4}\cos(\omega_c + \omega_m)t + \frac{A}{4}\cos(\omega_c - \omega_m)t$$

Equation 2 describes a DC sideband at $\omega_m$, a carrier band at $\omega_c$, and two carrier sidebands at $\omega_c-\omega_m$ and $\omega_c+\omega_m$ which correspond to DC sideband 2040, a carrier 2060, and sidebands 2050 and 2070 as shown in graph 2000. In Equations 1 and 2, t is time, i(t) is detector output current as a function of time, $\omega_c$ is carrier angular frequency, $\omega_m$ the modulation angular frequency, and A is the envelope amplitude. In further embodiments detector output could be a voltage, another electrical signal, an optical signal, or a magnetic signal, for example, or some combination of these and/or other outputs.

Figure 3:
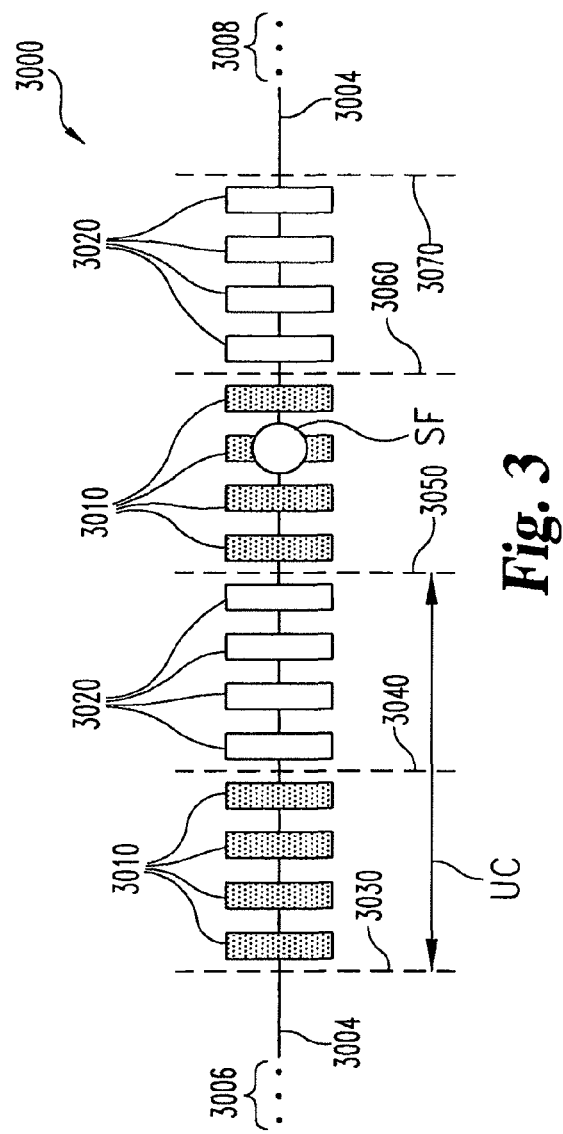
FIG. 3 shows a distribution of elements according to an embodiment of the present invention.

With reference to FIG. 3 there is shown a distribution of elements 3000 including elements 3010 and 3020. Elements 3010 and 3020 are distributed about reading pathway 3004 which is defined on a substrate. As shown by dashed lines 3030, 3040, 3050, 3060, and 3070, elements 3010 and 3020 are arranged in alternating groups of four. As shown by ellipses 3006 and 3008 this pattern can continue beyond the segment illustrated in FIG. 3 with the groups of four elements alternating as described above. A unit cell includes a group of four elements 3010 and a group of four elements 3020 as is indicated by arrow UC between dashed lines 3030 and 3050. Scanning footprint SF travels along reading pathway 3004 to scan the distribution of elements 3000. Additional embodiments include alternating groups of different numbers, for example, one, two, three, five or more, and corresponding different sizes of unit cells.

Elements 3010 include specific analyzer molecules which selectively bind with a target analyte and elements 3020 include nonspecific analyzer molecules which do not selectively bind with a target analyte but may exhibit similar binding properties with respect to other molecules. In a preferred embodiment according to the present invention, elements 3010 include specific antibodies immobilized about their surfaces, for example, as a monolayer, fractional monolayer, partial monolayer, or near monolayer, and elements 3020 include similarly immobilized nonspecific antibodies. For example, if an assay is to be conducted to identify a particular mouse protein the specific antibody could be goat anti-mouse IgG (the antibody to the mouse protein produced by a goat) and the nonspecific antibody could be goat anti-rat IgG (the antibody to an analogous rat protein produced by a goat). The goat anti-mouse IgG will selectively bind the mouse protein while the goat anti-rat IgG will not bind with it or will have a substantially lesser binding affinity, however, both IgGs exhibit similar nonspecific background binding with molecules other than the target analyte. In additional embodiments the non-specific protein could be a non-IgG, for example, casein or bovine serum albumin (BSA). These proteins could be used to test general protein-protein background, and could be used to test for systematics that are common to both groups of immobilized molecules. In further embodiments the specific analyzer molecules could be a cDNA that is complimentary to the target DNA, and the non-specific group could be a statistically similar, but not identical, cDNA. Additional embodiments cal include specific and non-specific aptamers. A variety of other specific and nonspecific antibody pairs may also be used, including those exhibiting varying degrees of similarity in nonspecific background binding and those not exhibiting similar nonspecific background binding. Furthermore, combinations of specific and nonspecific analyzer molecules other than antibodies may also be used. Additionally, nonspecific analyzer molecules may be omitted entirely in which case elements 3020 would not include immobilized molecules. These alternative exemplary embodiments and others can be used in connection with the present embodiment and also in connection with the other embodiments including those described elsewhere herein.

Distribution of elements 3000 is one example of differential encoding or envelope modulation of bimolecular information. According to a preferred embodiment of the present invention, distribution of elements 3000 is on a bio-CD where elements 3010 and 3020 are interferometric microstructures formed on a surface of the bio-CD, and reading pathway 3004 is one of a number of a substantially concentric circular tracks. As described above, elements 3010 on the track are active (carrying a specific biological analyzer molecule) and elements 3020 are inactive (carrying nonspecific molecules, no molecules, or inert molecules that may be comparable in size with the analyzer molecule). In this 4 on/4 off format, the carrier frequency corresponds to the positioning of each individual one of elements 3010 and 3020, and the detection frequency corresponds to the repeat period of the unit cell UC which is every eight elements. Thus, the detection frequency is equal to one-eighth of the carrier frequency. At disk rotation speeds of 6000 rpm (100 Hz) and 1024 elements per track, the carrier frequency is approximately 100 kHz and the detection frequency is approximately 12.5 kHz. A wide variety of other bimolecular platforms, scanning rates, and element distributions including, for example, those described herein, are contemplated and can result in a variety of other carrier frequencies and detection frequencies.

According to a preferred embodiment of the present invention, an optical detection system including two phase-locked loops in series, with the front end referenced to the carrier frequency, and the back end referenced to the unit cell can be used to scan a bio-CD having distribution of elements 3000 with a laser. Differential encoding of distribution of elements 3000, for example as described above and elsewhere herein, can preferably reduce susceptibility to laser intensity drift or disk wobble by subtracting out these and other system drifts and biases, and can preferably directly subtract non-specific background binding, for example if the off region is printed with nonspecific antibody. One example of a detection system according to a preferred embodiment of the present invention can be found in U.S. Pat. No. 6,685,885 which is hereby incorporated by reference. This detection system could also be any other detection system responsive to electromagnetic waves including for example those described elsewhere herein.

According to a preferred embodiment of the present invention the detection system can utilize phase quadrature interferometric techniques. Examples of phase quadrature interferometric techniques include the micro-diffraction quadrature class ("MD-class") and adaptive optic quadrature class ("AO-class") as described in U.S. application Ser. No. 10/726,772 filed on Dec. 3, 2003 entitled "Adaptive Interferometric Multi-Analyte High-Speed Biosensor" (published on Aug. 26, 2004 as U.S. Pub. No. 2004/0166593), the contents of which are incorporated herein by reference. Other examples of phase quadrature interferometric techniques include the phase-contrast quadrature class ("PC-class") as described in U.S. Provisional Patent Application No. 60/649, 070, filed Feb. 1, 2005, entitled "Phase-Contrast Quadrature For Spinning Disk Interferometry And Immunological Assay", U.S. Provisional Patent Application No. 60/755,177, filed Dec. 30, 2005, entitled "Phase-Contrast BioCD: High-Speed Immunoassays at Sub-Picogram Detection Levels", and U.S. application Ser. No. 11/345,462 being filed the same day as the present application that claims priority to these two provisional applications and entitled "Method And Apparatus For Phase Contrast Quadrature Interferometric Detection Of An Immunoassay." The disclosure of the utility application being filed on the same day as the present application is incorporated herein by reference. Additionally, further embodiments of the present invention include detection systems adapted to utilize surface plasmon resonance or SPR, fluorescence, resonance and other techniques in which high frequency modulation in time or space originates from analyte bound to a solid support with a spatial frequency that is scanned to produce a sideband indicating the presence of the analyte. Still other preferred embodiments of the present invention include detection platforms for use in these and other detection systems which include distributions of targets including analyzer molecules which produce sideband signals that depend upon modulation indicative of the presence of an analyte.

Figure 4:
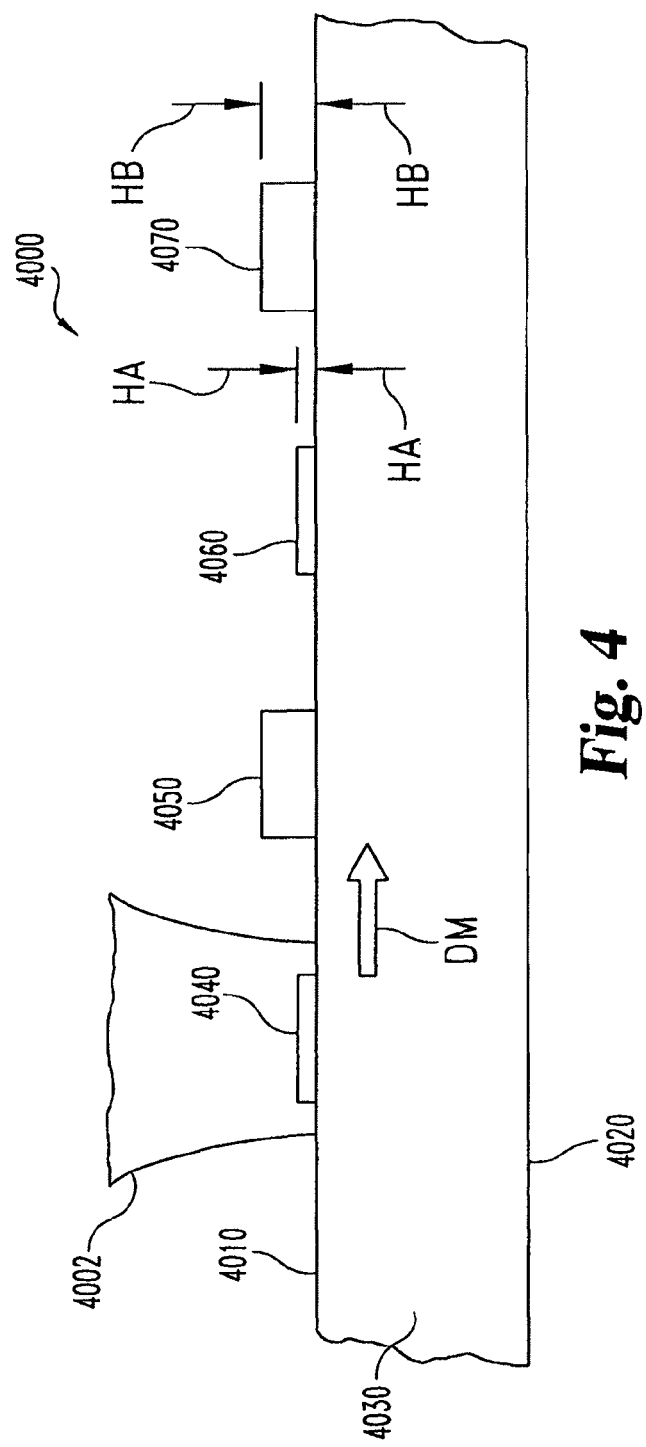
FIG. 4 shows a distribution of elements according to an embodiment of the present invention.

With reference to FIG. 4 there is shown a biosensor platform 4000 including a substrate 4030 having an upper surface 4010 and lower surface 4020. Interferometric elements 4040, 4050, 4060, and 4070 are formed on the upper surface 4010 of substrate 4030. Platform 4000 may also include additional interferometric elements in addition to those shown in the portion of platform 4000 illustrated in FIG. 4. A laser beam 4002 having wavelength λ scans the interferometric elements 4040, 4050, 4060, and 4070 in the direction indicated by arrow DM. Elements 4040 and 4050 include specific analyzer molecules immobilized about their scanned surfaces and elements 4060 and 4070 include nonspecific analyzer molecules immobilized about their scanned surfaces. These specific and nonspecific analyzer molecules can be, for example, the same or similar to those described above in connection with FIG. 3 and elsewhere herein. This configuration of specific and nonspecific analyzer molecules of biosensor platform 4000 is another example of differential encoding according to a preferred embodiment of the present invention. In one preferred embodiment of the present invention platform 4000 is a micro-diffraction bio-CD and elements 4040, 4050, 4060, and 4070 are radial spokes distributed about the surface of the bio-CD. Platform 4000 can also be any of various other biosensor platforms including, for example, those described herein.

Biosensor platform 4000 is one example of carrier suppression according to a preferred embodiment of the present invention. Elements 4060 and 4040 have a height illustrated by arrows HA and elements 4050 and 4070 have a height illustrated by arrows HB. Height HA is about λ/8 and height HB is about 3λ/8. Successive scanning of elements alternating between height HA and HB flips the phase quadratures detected for successive elements. This results in a modulation at about twice the amplitude as compared to a platform having interferometric elements with substantially uniform element heights. The carrier is suppressed by an approximately π phase difference between phase quadrature signals detected for successive elements. Carrier suppression may be useful in a variety of circumstances. In one example, where carrier side bands are weak relative to the carrier, carrier noise can impact detection. In another example where carrier sidebands overlap with the carrier, carrier noise can also impact detection. Carrier wave suppression can preferably increase the ratio of signal to noise. Complete carrier suppression or double sideband detection may be used to improve the signal to noise ratio of detection in these and other situations. Partial carrier suppression may also improve the signal to noise ratio of detection in these and other situations. Carrier wave suppression can also be accomplished in other manners, for example, fabrication of disk structures and reflectivities relative to beam width, through use of a clipper circuit that clips the high signal detected from a land of a detection platform, or through use of a filter, for example a band stop filter.

Figure 5:
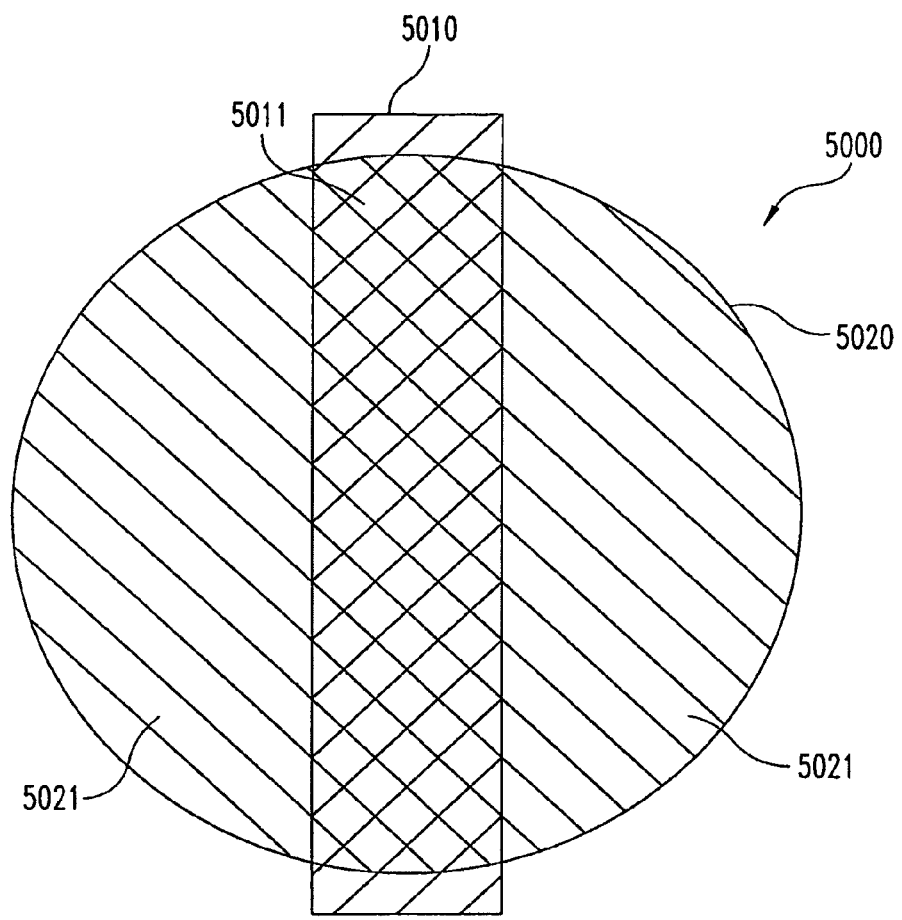
FIG. 5 shows scanning of an element according to an embodiment of the present invention.

With reference to FIG. 5 there is shown an example of a scanning 5000 during which footprint 5020 passes over element 5010. Areas 5021 are the areas of the scanning footprint not over element 5010 and area 5011 is the area in which scanning footprint 5020 overlaps element 5010. According to a preferred embodiment element 5010 is a gold microdiffraction element placed on a partially reflecting substrate. This embodiment allows carrier suppression by the total power reflected from the element being equal to the total power reflected under the condition of quadrature which removes the large modulation caused by the approximately 50% amplitude modulation of a micro diffraction bio-CD. This effect can be illustrated through the following equations. The total electrical (far) field is given by Equation 3:

$$E_T = \frac{E_0}{\sqrt{A}}[r_L A_L + r_r A_r e^{i\phi}]$$

The total reflected intensity is given by Equation 4:

$$I_T = \frac{E_0^2}{A}[R_L A_L^2 + R_r A_r^2 + 2r_L r_r A_L A_r \cos\phi]$$

Under the condition of Land: $\Phi=0$, $A_L=A$ and $A_r=0$. Thus, intensity reflected by land is given by Equation 5:

$$I_L = I_0 R_L$$

Under the condition of Quadrature: $\Phi=\pi/2$. Thus, the reflected intensity under a condition of quadrature is given by Equation 6:

$$I_Q = \frac{E_0^2}{A}[R_L A_L^2 + R_r A_r^2]$$
$$= I_0[R_L a_L^2 + R_r a_r^2]$$

where $a_i$ is the area fraction, and $a_L + a_r = 1$. Conditions of balanced operation are given by Equations 7 and 8:

$$I_Q = I_L$$

$$R_L a_L^2 + R_r a_r^2 = R_L$$

The solution of which are given in Equations 9 and 10:

$$\frac{1-a_L}{1+a_L} = \frac{R_L}{R_r}$$

$$a_L = \frac{1 - \frac{R_L}{R_r}}{1 + \frac{R_L}{R_r}}$$

For Equations 3-10, $I_r$ is the total reflected intensity, $I_L$ is the intensity reflected by land, $I_O$ is the incident reflected intensity, $I_Q$ is the reflected intensity under a condition of quadrature, $E_o$ is the reflected field, A is the total area, $A_L$ is area 5021, $A_r$ is area 5011, $a_L$ is $A_L$ divided by the area of the beam footprint, $a_R$ is $A_L$ divided by the area of the element 5010 intersecting element 5020, $R_L$ is $|r_L|^2$, $R_r$ is $|r_r|^2$ and $\Phi$ is the phase difference between reflected components of the laser. Thus, if the partially reflective substrate is silicon, for example, which has $R_L$=32% and $R_r$=98%, then $a_L$=51% and $a_r$=49%.

Figure 6:
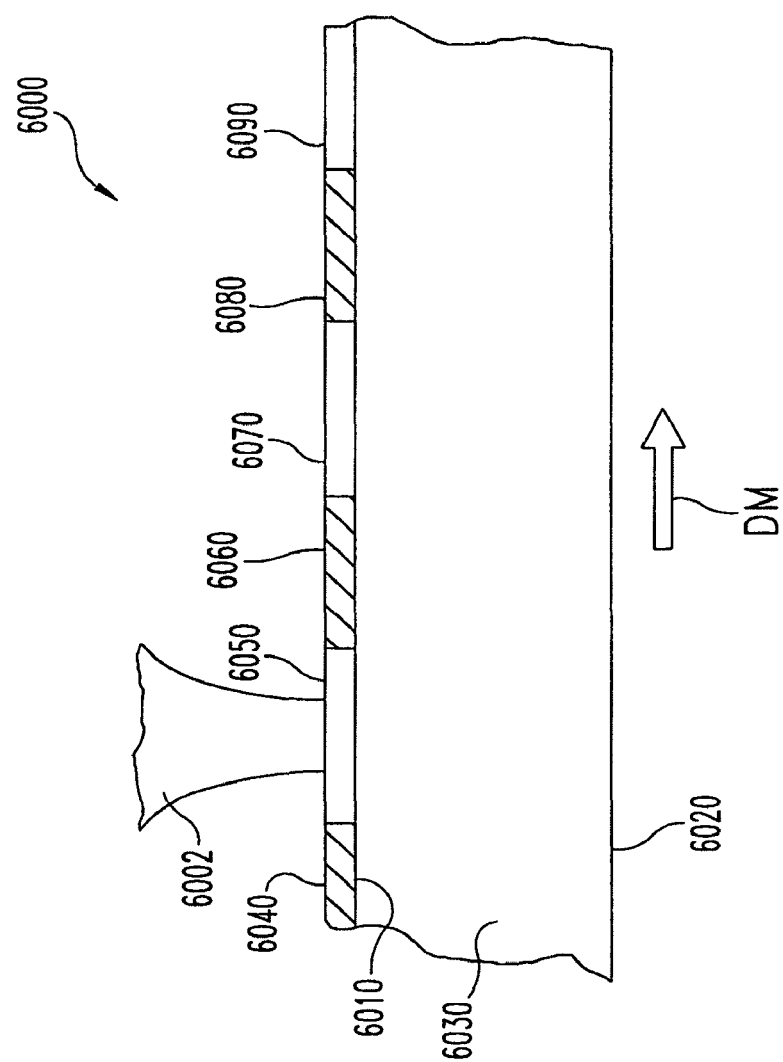
FIG. 6 shows a distribution of elements according to an embodiment of the present invention.

With reference to FIG. 6 there is shown a biosensor platform 6000 including substrate 6030 having an upper surface 6010 and a lower surface 6020. Upper surface 6010 includes analyzer molecules 6040, 6050, 6060, 6070, 6080 and 6090 immobilized about surface 6010. Analyzer molecules 6040, 6060, and 6080 are specific analyzer molecules for selectively binding a particular analyte and analyzer molecules 6050, 6070 and 6090 are nonspecific analyzer molecules. The specific and nonspecific analyzer molecules can be, for example, the same or similar to those described elsewhere herein. FIG. 6 shows one example of an alternating pattern of specific and nonspecific analyzer molecules. Laser beam 6002 scans the analyzer molecules in the direction indicated by the arrow DM which is preferably accomplished by rotating the platform 6000 but could also be accomplished by other movement of platform 6000 or by movement of beam 6002. According to a preferred embodiment of the present invention platform 6000 is a phase contrast bio-CD or an adaptive optical bio-CD and analyzer molecules 6040, 6050, 6060, 6070, 6080 and 6090 are radial spokes or other patterns of analyzer molecules, however, platform 6000 could also be another kind of bio-CD or other platform including, for example, those described elsewhere herein.

During scanning of platform 6000 by laser beam 6002 signal phase modulation depends only upon the binding differences between the specific and nonspecific analyzer molecules. For example, nonspecific binding that is common to both the types of analyzer molecules is not imparted onto the signal beam or has minimal impact on the signal beam. The detected signal is therefore independent of nonspecific binding. In this embodiment there is no signal detected at or about the carrier frequency and only the modulation caused by binding of the specific analyte and the specific analyzer molecule is detected. This is one example of differential encoding including carrier wave suppression and double sideband detection.

Figure 7:
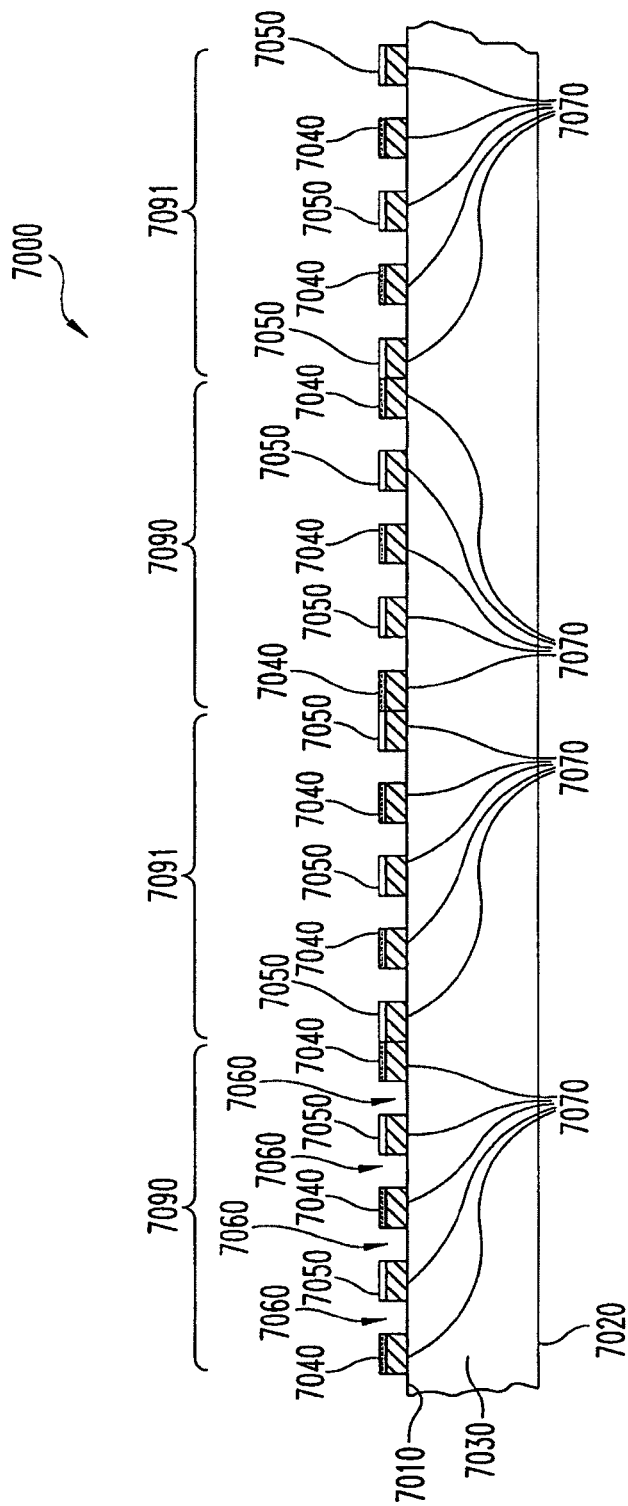
FIG. 7 shows a distribution of elements according to an embodiment of the present invention.

With reference to FIG. 7 there is shown a biological analyzer platform 7000 including substrate 7030 including upper surface 7010 and lower surface 7020. Interferometric elements 7070 are distributed about upper surface 7010 and are spaced apart by gaps 7060. Interferometric elements 7070 include specific biological analyzer molecules 7040 and nonspecific biological analyzer molecules 7050 immobilized about their surfaces which can be the same or similar to those described elsewhere herein. Groups of the interferometric elements and analyzer molecules 7090 and 7091 are also shown. Groups 7090 and 7091 have patterns of specific and nonspecific analyzer molecules that are at spatial frequencies with a $\pi$ phase difference, that is, the positions of specific and nonspecific analyzer molecules are flipped between groups 7090 and 7091. Platform 7000 is preferably an adaptive optical bio-CD, however, platform 6000 could also be any other type of biosensor platform or another type of bio-CD including, for example, those described elsewhere herein.

During scanning of platform 7000 by a laser beam the phase of the carrier is periodically flipped by $\pi$ for successive groups 7090 and 7091. The effect of the phase flipping of the carrier is that the carrier is suppressed in the power spectrum and the modulation due to binding of a specific analyzer molecule to the specific antibodies is detectable at carrier sidebands. This is one example of differential encoding including carrier wave suppression and double sideband detection.

According to a preferred embodiment modulated signals are detected within a detection bandwidth $\Delta f_d$. Narrow bandwidths reject more noise, but the detection bandwidth should preferably not be smaller than the signal bandwidth, otherwise a part of the signal is rejected with the noise. The signal bandwidth is determined by the relationship described by Equation 11:

$$\Delta \omega_s \Delta \tau = 1$$

where $\Delta \omega_s = 2\pi \Delta f_s$, $\Delta f_s$ is the signal bandwidth, and $\Delta \tau$ is the duration of either a contiguous part of the signal, or the duration of the signal detection measurement. In preferred embodiments utilizing bio-CDs, the carrier frequency, $f_{carrier}$, is set by the rotation frequency of the bio-CD, $f_{disk}$, and by the number of spokes, targets, or interferometric elements, N, around a specified circumference as described by Equation 12:

$$f_{carrier} = N f_{disk}$$

The signal bandwidth $\Delta f_s$ is described by Equation 13:

$$\Delta f_s = \frac{f_{disk}}{2\pi}$$

The relative signal bandwidth $\Delta f_{rel}$ is described by Equation 14:

$$\Delta f_{rel} = \frac{\Delta f}{f_{carrier}}$$

For a single continuous track around a circumference, the relative bandwidth $\Delta f_{rel}$ is described by Equation 14:

$$\Delta f_{rel} = \frac{1}{2\pi \Delta \tau f_{carrier}} = \frac{f_{disk}}{2\pi N f_{disk}} = \frac{1}{2\pi N}$$

If a circumference is divided into S equal arcs of M spokes, the relative bandwidth increases by a factor of S as described by Equation 15:

$$\Delta f_{rel}^S = \frac{N}{M} \Delta f_{rel} = S \Delta f_{rel}$$

Thus, for example, if N=1024, and S=16, the relative bandwidth is 0.25%. If $f_{disk}$=100 Hz, then $f_s$=100 kHz, $\Delta f_s$=16 Hz and $\Delta f_{s\ rel}$=256 Hz. These relations suggest that S up to 128 segments or more is clearly a possible scenario for homogeneous bandwidths for which $\Delta f_s$=2 kHz and $\Delta f_{s\ rel}$=2%.

The foregoing example describes the case of homogeneous signal bandwidth. Signal bandwidths in practice are generally larger than the homogeneous bandwidths. These arise, for example, from frequency instability, which in the bio-CDs is from inhomogeneities in the fabricated or printed spokes. If the placement of the spokes is only accurate to 10 microns, then the bandwidth of the repetitive spoke pattern is approximately 4 kHz with a relative bandwidth of 4%. This inhomogeneous signal bandwidth sets the correct detection bandwidth for the bio-CDs. The number of segments can be increased to increase the homogeneous bandwidth until it is equal to the inhomogeneous bandwidth to the relationships described by Equations 16 and 17:

$$\Delta f^S = \Delta f_{in\,hom}$$
$$BW = \sqrt{2\Delta f_{in\,hom}}$$

For detection bandwidth BW, this sets the maximum segment number according to Equation 18:

$$S = \sqrt{2\pi N}\left(\frac{BW}{f_{carrier}}\right)$$

which for BW=3 kHz and $f_{carrier}$=100 kHz for N=1024, this sets the maximum S=136.

The ability to support segments suggests a disk array layout that segments the printed antibodies into wells. For N wells on a disk or S segments, the size of a well and its radial thickness are given by Equations 19 and 20:

$$a = rd\theta dr = r\frac{2\pi}{S}dr = A/N$$
$$dr = \frac{AS}{2\pi rN} = \frac{(R_2^2 - R_1^2)S}{2rN}$$

where a is the area of a well, r is radius, dr is radial thickness of a well, θ is angular position, dθ is well arc length, A is the area of the annular region between radii $R_2$ and $R_1$, N is number of wells, S is the number of segments, $R_1$ is the inner radius, and $R_2$ is the outer radius.

Figure 8:
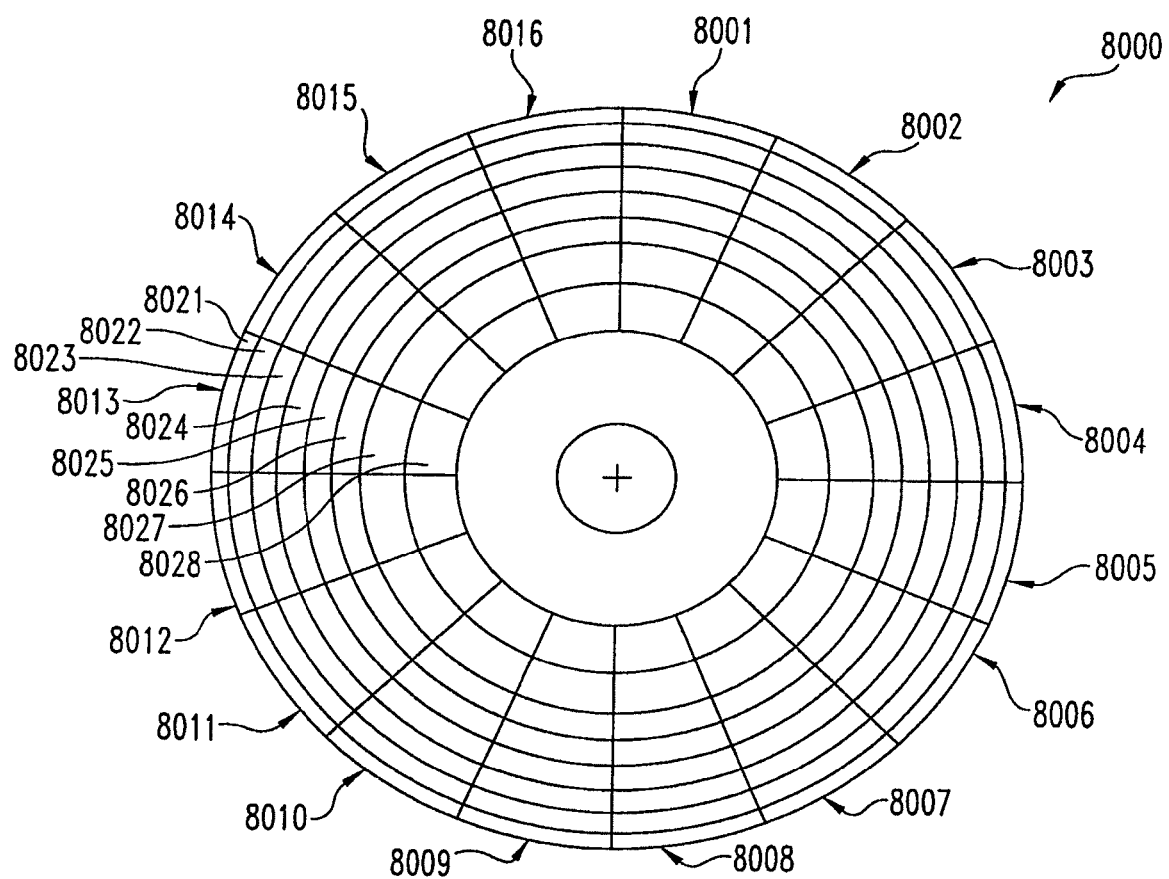
FIG. 8 shows a bio-CD according to an embodiment of the present invention.

With reference to FIG. 8 there is shown a bio-CD 8000 according to one embodiment of the present invention. Bio-CD 8000 is a 100 mm diameter disk or silicon wafer, however, any other dimension disk, wafer chip or other substrate or platform could also be used. Bio-CD 8000 includes sectors 8001, 8002, 8003, 8004, 8005, 8006, 8007, 8008, 8009, 8010, 8011, 8012, 8013, 8014, 8015, and 8016. Bio-CD 8000 further includes substantially concentric tracks of wells 8021, 8022, 8023, 8024, 8025, 8026, 8027, and 8028. Bio-CD 8000 has S=16 sectors, N=128 then T=8 (tracks) and the inner track radius and radial thicknesses are given in Table I:

| Track Number | Inner Track Radius (millimeters) | Radial Thickness dr (millimeters) |
|---|---|---|
| 8028 | 20 | 6.56 |
| 8027 | 26.56 | 4.94 |
| 8026 | 31.50 | 3.60 |
| 8025 | 35.10 | 3.39 |
| 8024 | 38.50 | 3.13 |
| 8023 | 41.63 | 2.93 |
| 8022 | 44.56 | 2.76 |
| 8021 | 47.33 | 2.62 |

Bio-CD 8000 is one example of an equal area well layout according to the present invention. Other layouts are also contemplated, for example, a 512 well layout with S=16, T=32, and any other combination of sectors and tracks. According to a preferred embodiment layouts are used which bring the aspect ratio of arc length and radial thickness closer to unity which simplifies fabrication. Fabrication of this and other embodiments of the present invention can include particular features for various classes of bio-CDs. For example, a micro-diffraction bio-CD can have radial spokes fabricated from gold across the entire disk, and wells defined by hydrophobic dams. A pin plotter or ink-jet printer modified from biochip array printers can be used to deposit an equal amount of analyzer molecules into each well. Different antibodies can be deposited which then self-immobilize on thiolated gold. In another example gel printing can be used. In another example, for adaptive optical bio-CDs and phase constant bio-CDs, spokes can be printed as inert protein, dams can be put into place and antibody deposited into the wells by pin array plotters or protein spotters.

With reference to FIGS. 9A, 9B, 10A, 10B and 11 there are shown bio-CDs 9000A, 9000B, 10000A, 10000B, and 11000 according to embodiments of the present invention where the wells are of equal area. In these embodiments, dr is held constant among the tracks, and ds=rdθ is also held constant. This leads to a varying dθ across the disk. In the preferred embodiment where well areas remain are equal, the radial width of each well is constant which simplifies design of the protein plotter, and optimal use of real-estate is made. This embodiment requires a carrier spoke number C to vary with radius, also causing the carrier frequency to vary with radius (for constant angular velocity). The relation of the spoke number is given by Equation 21:

$$C = \frac{2\pi r}{\Lambda}$$

where Λ is the spatial period, usually Λ=2w, where w is the beam waist. For a beam waist of 20 microns and Λ=40 microns, this gives the number of spokes as a function of radius C=3000 at r=20 mm and C=8000 at r=50 mm. The carrier frequencies are 300 kHz and 800 kHz, respectively.

For N wells, the area of each well is given by Equation 22:

$$a = rd\theta dr = A/N$$

The aspect ratio $a_r$ is set by the Equation 23:

$$rd\theta = a_r dr$$

The radial widths and angular widths are given by Equation 24:

$$dr = \sqrt{\frac{A}{a_r N}} \text{ and } d\theta = \frac{1}{r}\sqrt{\frac{a_r A}{N}}$$

Figure 9B:
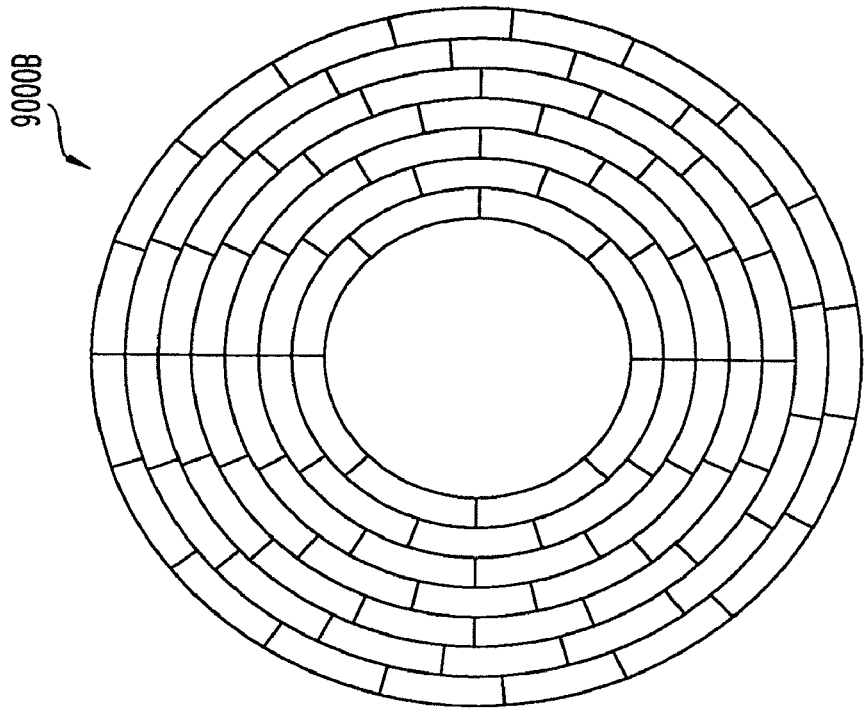
FIG. 9B shows a bio-CD according to an embodiment of the present invention.
Figure 9A:
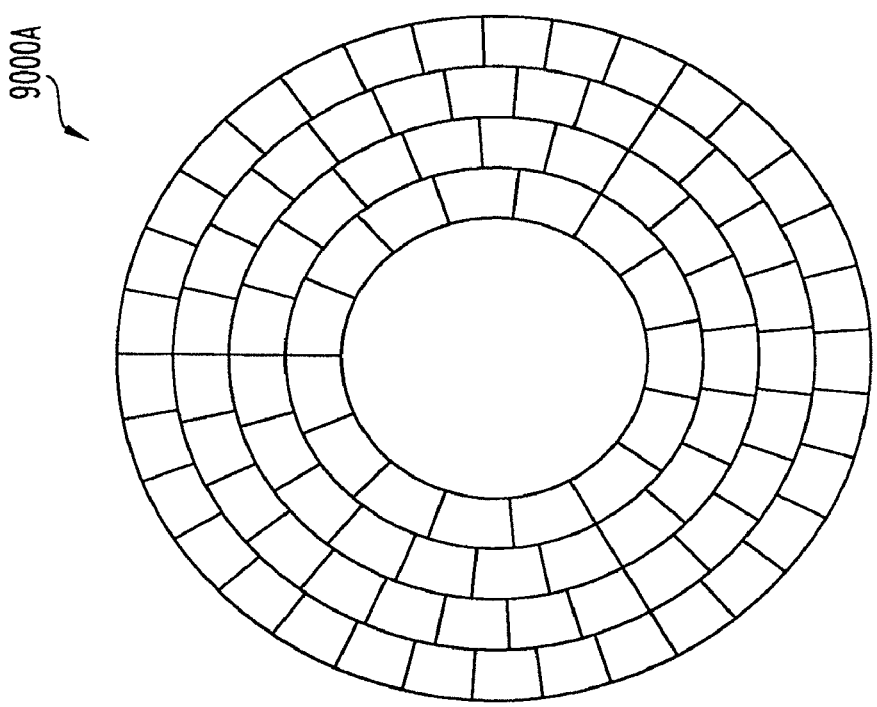
FIG. 9A shows a bio-CD according to an embodiment of the present invention.
Figure 10B:
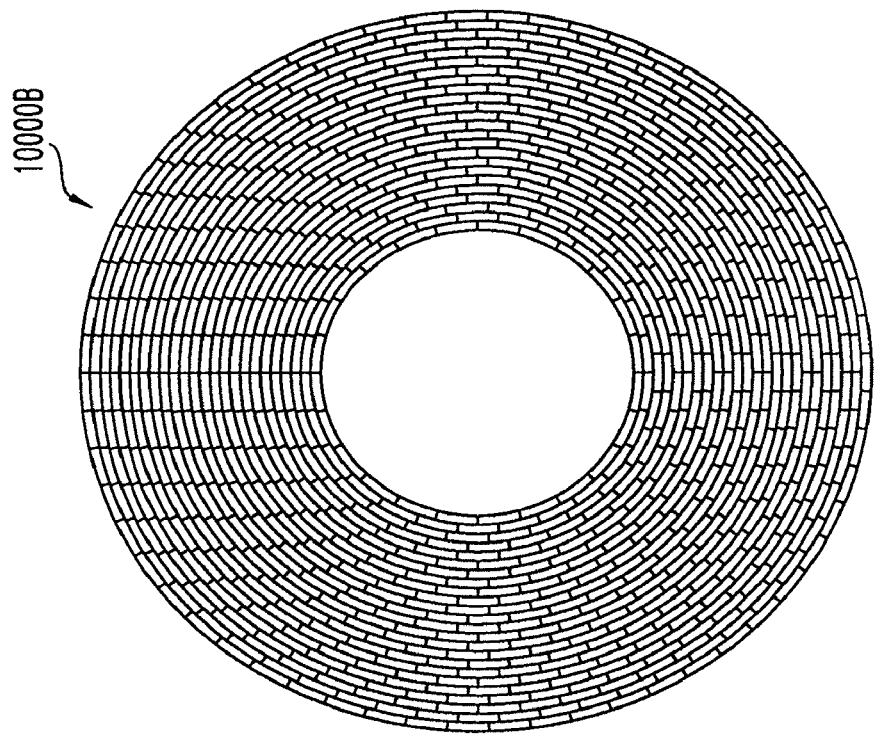
FIG. 10B shows a bio-CD according to an embodiment of the present invention.
Figure 10A:
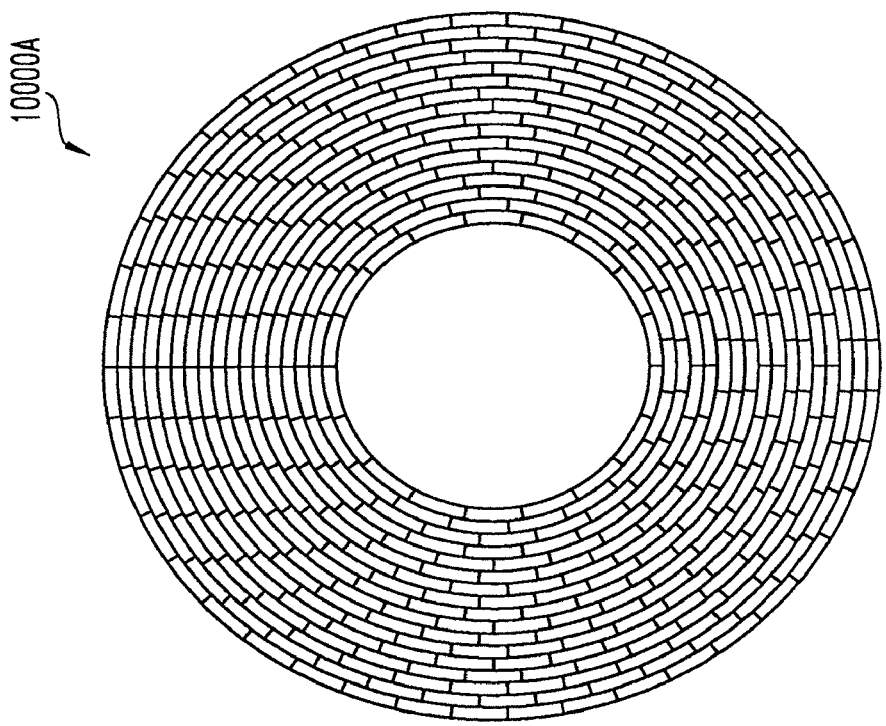
FIG. 10A shows a bio-CD according to an embodiment of the present invention.
Figure 11:
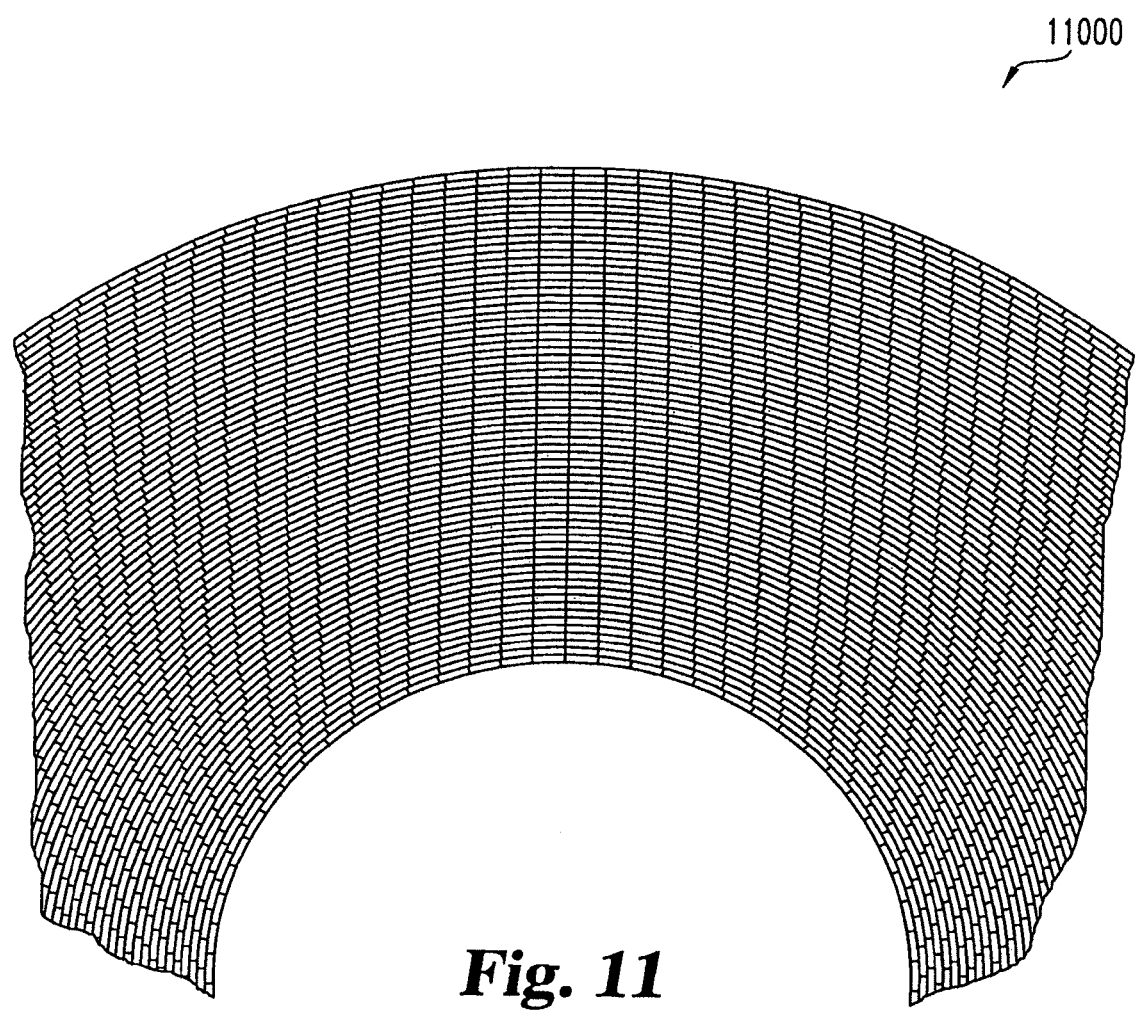
FIG. 11 shows a bio-CD according to an embodiment of the present invention.

FIG. 9A shows a 96 well disk with an aspect ratio of 1 and dr=7.5 mm, a=61 mm², T=4, $S_i$=15, and $S_o$=33. FIG. 9B shown a 96 well disk with an aspect ratio of 4 and dr=4.3 mm, a=64 mm², T=7, $S_i$=8, and $S_o$=19. The well in FIGS. 9A and 9B areas are approximately 0.6 cm². FIG. 10A shows a 512 well disk with an aspect ratio of 4, dr=1.76 mm, a=12.7 mm², T=17, $S_i$=17, and $S_o$=42, FIG. 10B shows a 1000 well disk with an aspect ratio of 4, dr=1.25 mm, a=6.4 mm², T=24, $S_i$=24, and $S_o$=59. FIG. 11 shows an 8000 well disk with an aspect ratio of 4, dr=0.45 mm, a=0.82 mm², T=66, $S_i$=69, and $S_o$=172. A variety of other disks with equal area wells and unequal well areas are also contemplated. In general, larger aspect ratios have narrower detection bandwidth, but more tracks with smaller track pitches.

Figure 12:
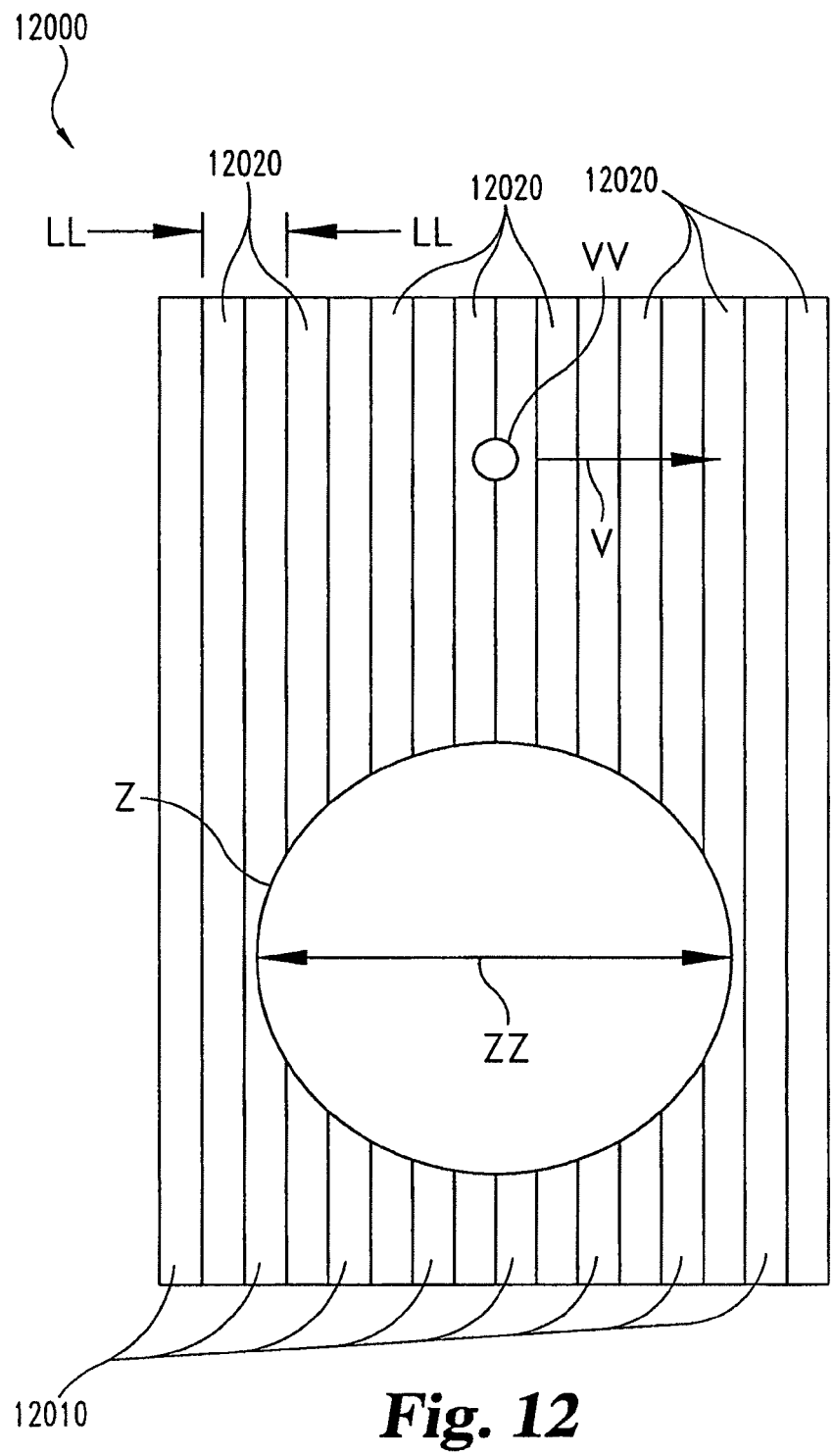
FIG. 12 shows scanning of elements according to an embodiment of the present invention.

With reference to FIG. 12 there are shown examples of scanning targets 12000. Targets 12000 are a periodically alternating pattern of targets including specific antibodies 12010 and targets including nonspecific antibodies or not including antibodies 12020. Specific and nonspecific antibodies are being immobilized about a substrate, for example, as described herein. After exposure to a sample including a specific target analyte, targets 12010 have the analyte bound to their analyzer molecules while targets 12020 exhibit little or no binding of the specific analyte. The period of the alternating pattern is shown by arrows LL, and the spatial frequency of the pattern is inversely proportional to its period as shown by Equation 25:

$$V_{spatial} = \frac{1}{\Lambda}$$

where $\Lambda$ is the spatial periodicity and $v_{spatial}$ is the spatial frequency.

During scanning targets 12000 are illuminated by a scanning footprint such as a laser spot. The scanning footprint could be, for example, focused laser spot vv which has a width $w_o$ less than spatial periodicity $\Lambda$ (preferably $w_o \ll \Lambda$) and moves relative to the targets 12000 with a velocity in the direction indicated by arrow v. Under these scanning conditions the spatial frequency $v_{spatial}$ is converted into temporal frequency on the transmitted or reflected beam as described by Equation 26:

$$f = V \cdot v$$

where f is the carrier frequency of phase or amplitude modulation.

The scanning footprint could also be, for example, broad area laser spot z which has a width $w_o$ greater than spatial periodicity $\Lambda$ (preferably $w_o \gg \Lambda$) and can be stationary or can move relative to the targets 12000 with a velocity V in the direction indicated by arrow v. When laser spot z is stationary and broadly illuminates the spatial frequency, then the spatial frequency leads to diffraction at specific angles as described by Equation 27:

$$\theta = \sin^{-1}\left(\frac{\lambda}{\Lambda}\right)$$

where $\lambda$ is the illumination wavelength, and $\Lambda$ is the spatial period. When laser spot z moves over to targets 12000, or targets 12000 move with velocity V, then the diffracted orders acquire a phase modulation that is time-periodic.

The foregoing examples illustrate how spatial frequencies on a scanning platform, for example a chip or disk, can be converted into temporal frequencies in a laser scanning system, and how the two types of frequencies can be combined when a laser probes more than one target on the platform.

Figure 13:
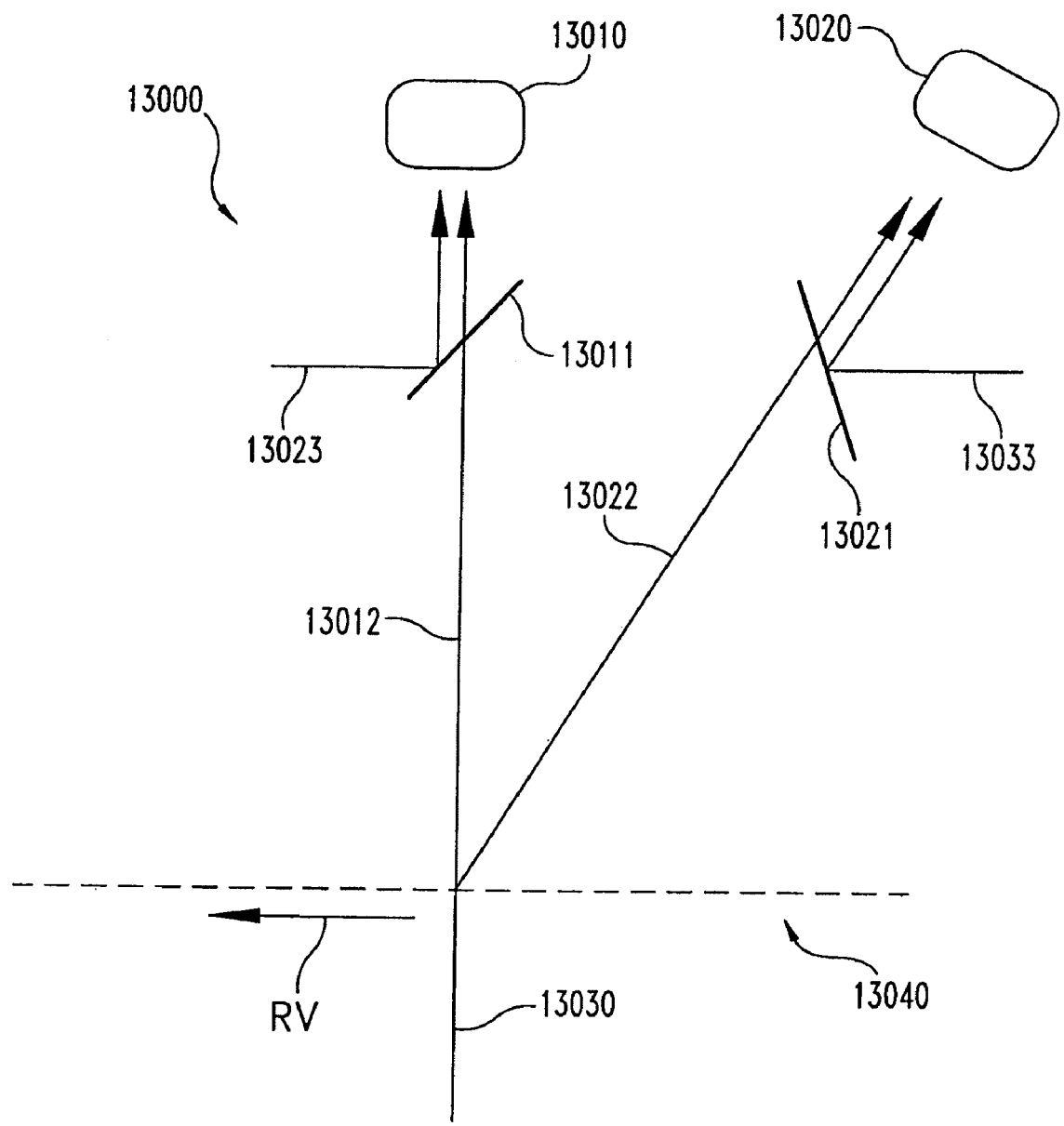
FIG. 13 shows a detection system according to an embodiment of the present invention.

With reference to FIG. 13 there is shown detection system 13000 which includes detector 13010 and detector 13020. Detectors 13010 and 13020 could be any detectors for detecting electromagnetic waves, for example optical detectors. System 13000 further includes probe beam 13030 which can be a focused probe beam or a broad area probe beam. Probe beam 13030 scans targets 13040 which move relative to beam 13030 with a relative velocity in the direction indicated by arrow RV. The scanning targets 13040 by beam 13030 results in a transmitted or reflected mode 13012 and a diffracted mode 13022. Mode 13012 is directed to detector 13010 and mode 13022 is directed to detector 13020. Reference beam 13023 is directed to detector 13010 and reference beam 13023 is directed to detector 13020. Reference beam 13023 is preferably maintained in a condition of phase quadrature relative to the transmitted mode 13012. Reference beam 13033 is preferably maintained in a condition of phase quadrature relative to diffracted mode 13022. System 13000 also includes beam splitters 13011 and 13021 which could also be adaptive optical beam combiners. Having a reference wave that is in phase quadrature with detected signal allows a small shift in the phase modulation of the signal to linearly proportional change in detected intensity allowing signal modulation per bound analyte molecule to be maximized. Reference beams 13033 and 13023 can be added before photodetectors or can be combined adaptively with signals. Reference beams 13033 and 13023 can arise from a diffracted spatial mode, for example, in the case of wavefront splitting, from free space, or from partial reflections, for example, in the case of amplitude splitting. It is also contemplated that detection system 13000 could include only one or the other of detectors 13010 and 13020 and their related beams and modes.

Figure 14:
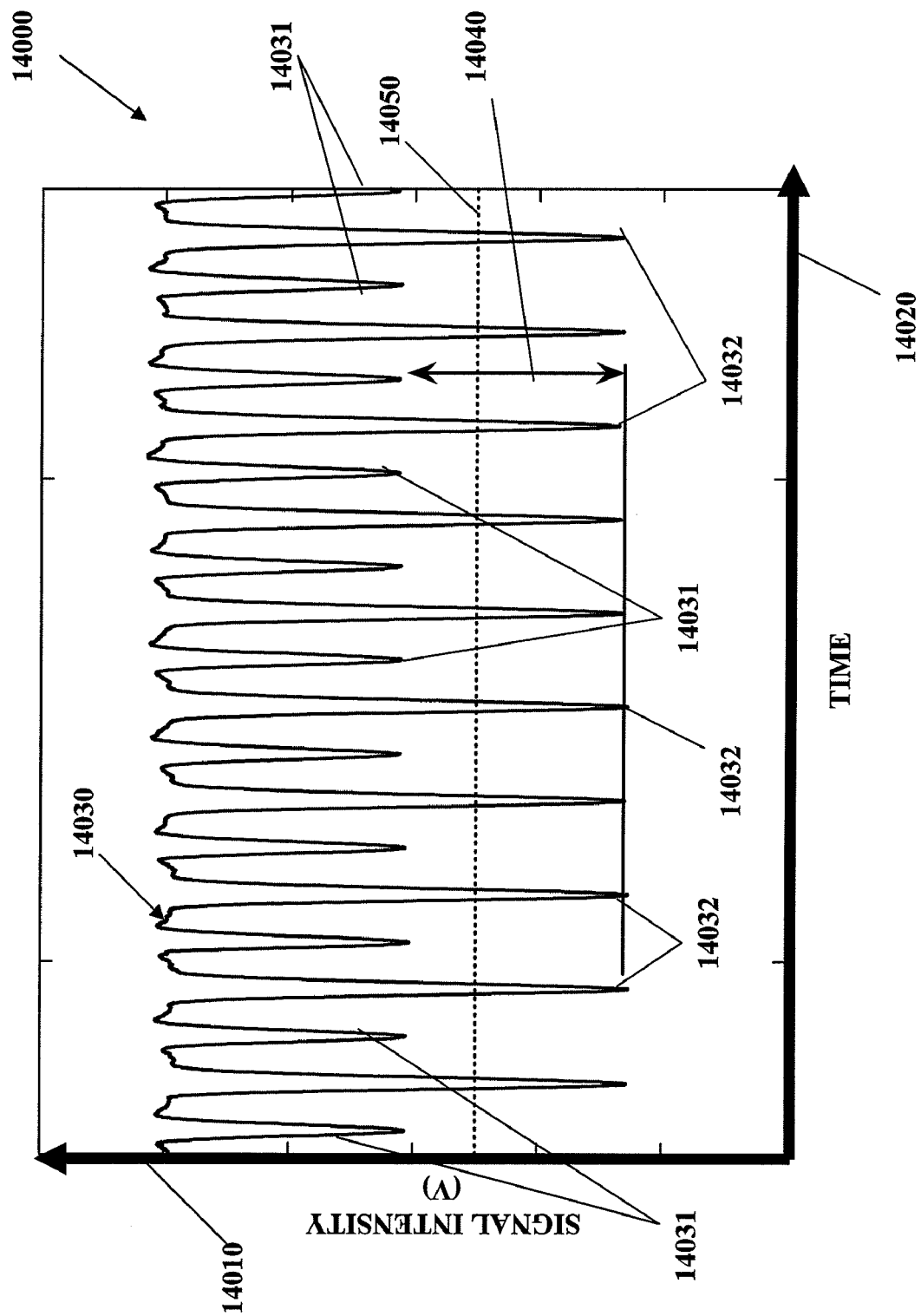
FIG. 14 shows a graph of time domain results of scanning a differentially encoded MD-class calibration disk.

Experimental demonstrations of several exemplary embodiments including carrier side band detection according to the present invention will now be described in connection with FIGS. 14-28. With reference to FIG. 14, there is shown graph 14000 with time increasing along its x axis as indicated by x axis arrow 1420 and signal intensity (voltage) increasing along its y axis as indicated by y axis arrow 14010. Graph 14000 further shows signal 14030 which is a voltage signal that varies with time. Signal 14030 results from the scanning of an MD-class calibration disk which was fabricated with 1024 gold spokes deposited radially on a dielectric substrate. The average (mean) spoke height was 80 nm. Of the 1024 spokes, 512 spokes were below the average height, 512 spokes were above the average height, and the spokes alternated between those above the average height and those below the average height.

Scanning the MD-class calibration disk produced signal 14030 which includes a series of alternating local minima 14031 and 14032 corresponding to and indicating the two spoke heights. The signal intensity difference between the alternating local minima 14031 and 14032 is illustrated by arrow 14040 and corresponds to a height difference of about 30 nm between alternating spokes. This height difference is representative of the height difference cause by certain target analytes to analyzer molecules. The signal level corresponding to the average spoke height of about 80 nm is indicated by dashed line 14050. The MD-class calibration disk thus provides a simulation of a differential encoding scheme whereby every other alternating spoke includes analyzer molecules that bind a target analyte and can be compared to a reference spoke. The fast relative comparison between the two types of spokes allows for significant noise reduction.

Figure 15:
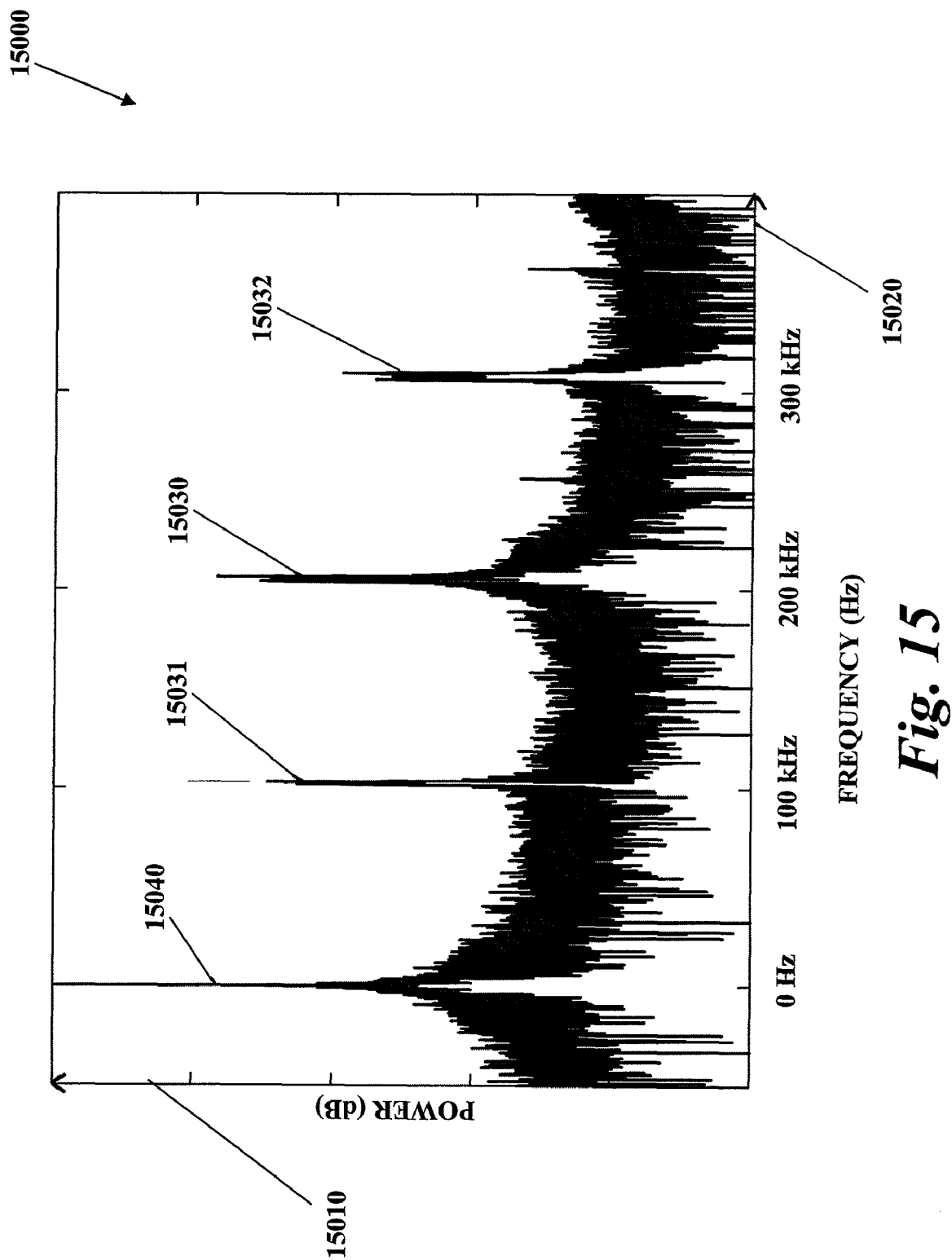
FIG. 15 shows a graph of frequency domain results of scanning a differentially encoded MD-class calibration disk.

With reference to FIG. 15 there is shown graph 15000 with frequency increasing along its x axis as shown by x axis arrow 15020 and power increasing logarithmically along its y axis as shown by y axis arrow 15010. Graph 15000 shows the frequency domain results of the scanning of the MD-class calibration disk described above in connection with FIG. 14. Graph 15000 shows carrier signal 15030 at 200 kHz, sideband signal 15031 at 100 kHz, and sideband signal 15032 at 300 kHz. Thus the sideband signals are present at half carrier frequency increments. A strong 1/f noise peak 15040 is present at zero frequency, and a significantly suppressed noise floor is present at the frequencies of carrier and sideband signals 15030, 15031 and 15032. The noise suppression by operating at this scanning rate is over 60 dB or 3 orders of magnitude better signal to noise ratio when compared to a static measurement at DC (zero frequency). This is a fundamental advantage to high speed repetitive sampling according to certain embodiments of the present invention.

Figure 16:
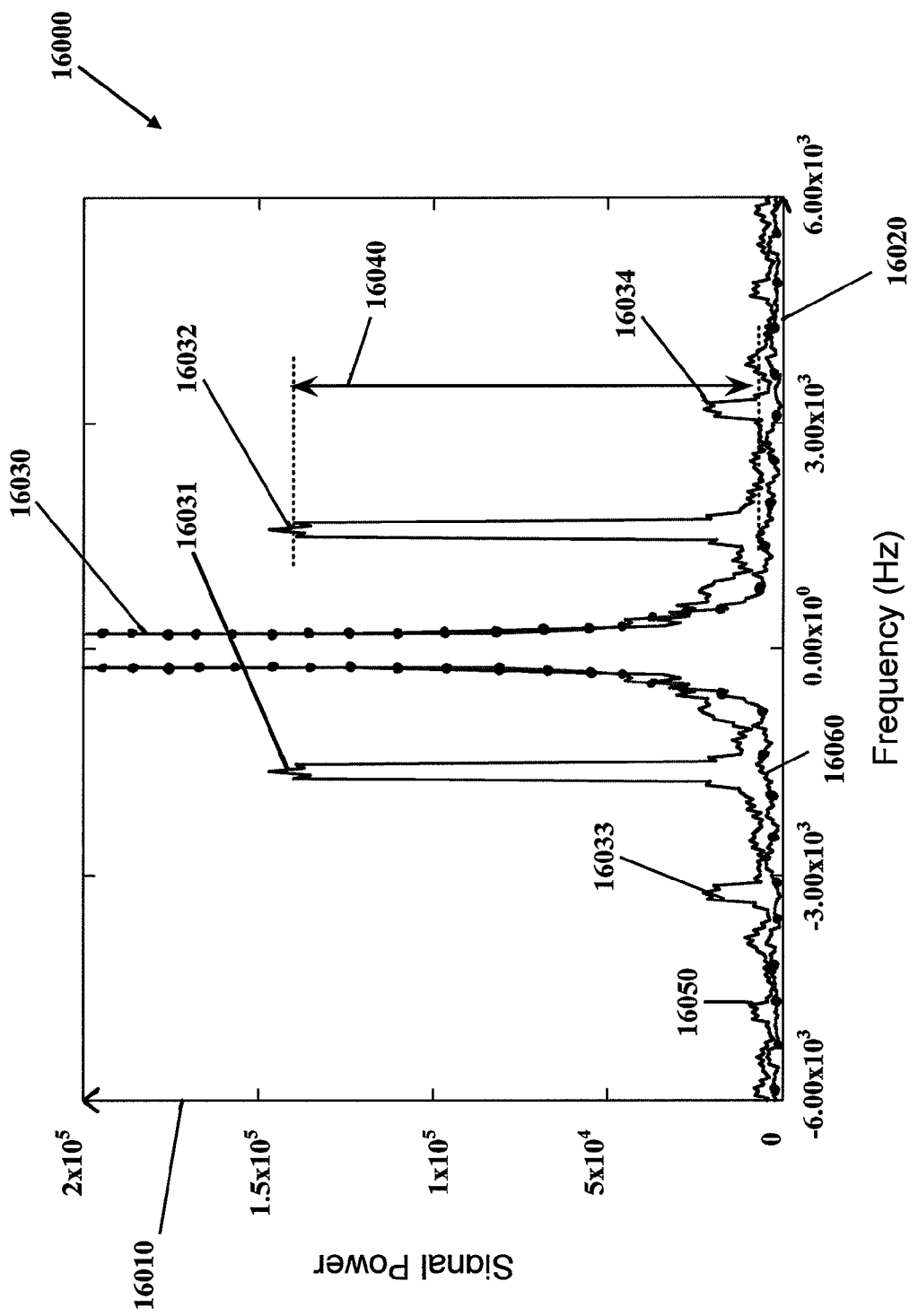
FIG. 16 shows a graph of frequency domain results of scanning a differentially encoded MD-class disk.

With reference to FIG. 16 there is shown graph 16000 with frequency increasing along its x axis as shown by x axis arrow 16020 and power increasing along its y axis as shown by y axis arrow 16010. Graph 16000 shows an example of protein side-band detection for an MD-class disk having proteins (in this case antibody IgG molecules) immobilized on a 1024-spoke disk with 64 segments composed of 8 elements with protein and 8 elements without. This created a disk with an alternating pattern of 8 gold spokes carrying protein followed by 8 bare gold spokes. This pattern repeated for a total of 64 segments each with a total of 16 elements divided into 8 with protein and 8 without. The proteins were patterned using a polydimethylsiloxane (PDMS) stencil on the disk. A control track which did not include printed protein was also included on the disk. The results of scanning the control track are indicated by dotted line 16060 and the results of scanning a track including the patterned protein are indicated by line 16050.

Graph 16000 shows 16030 the 1/f noise at DC and two DC sideband signals 16031 and 16032. A carrier frequency signal (not shown) is present at about 100 kHz. The presence of protein is detected as a 1/64 harmonic of the carrier frequency at about 1.6 kHz as shown by signal 16032 and also by signal 16031 at about −1.6 kHz. A second harmonic signal 16034 and 16033 is also present at 1/32 the carrier frequency and is caused by slight asymmetry in the deposition of the proteins. A comparison of protein track signal 16050 and signal 16060 of a control track containing no protein illustrates the strong effect of the protein in producing sideband signals with a 20:1 signal to noise ratio as indicated by arrow 16040.

Figure 17:
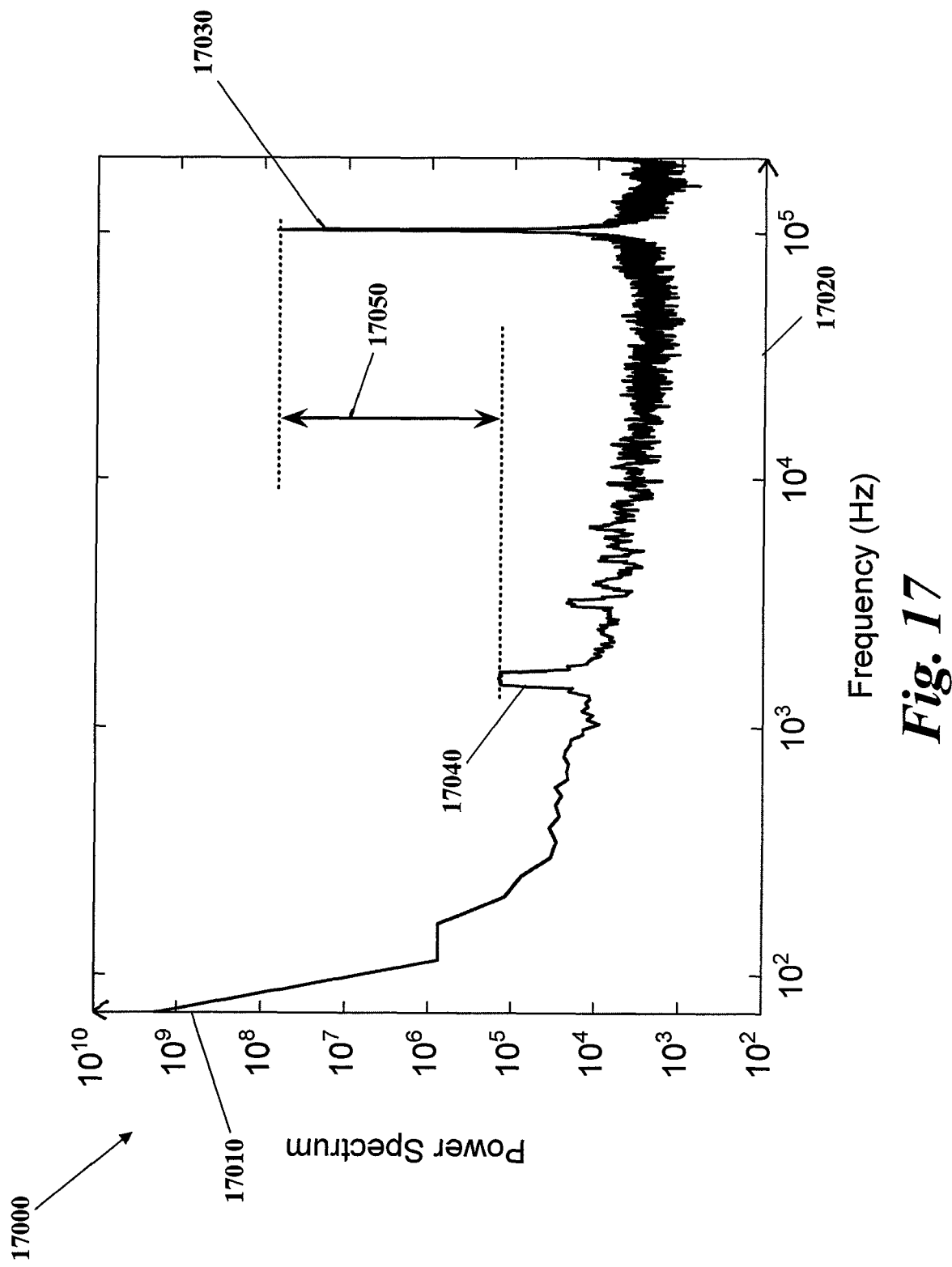
FIG. 17 shows a graph of frequency domain results of scanning a differentially encoded MD-class disk.

With reference to FIG. 17 there is shown graph 17000 with frequency increasing along its x axis as shown by x axis arrow 17020 and power spectrum increasing logarithmically along its y axis as shown by y axis arrow 17010. Graph 17000 presents average values for scanning of six tracks of the MD-class disk which is described above in connection with FIG. 16. Graph 17000 shows a comparison of 1/64 harmonic signal 17040 at about 1.6 kHz, which is generated by and indicates the presence of protein, and carrier signal 17030. As illustrated by arrow 17050, the protein modulation is about 4.6% of the carrier wave, which is consistent with a monolayer of immobilized protein.

Figure 18:
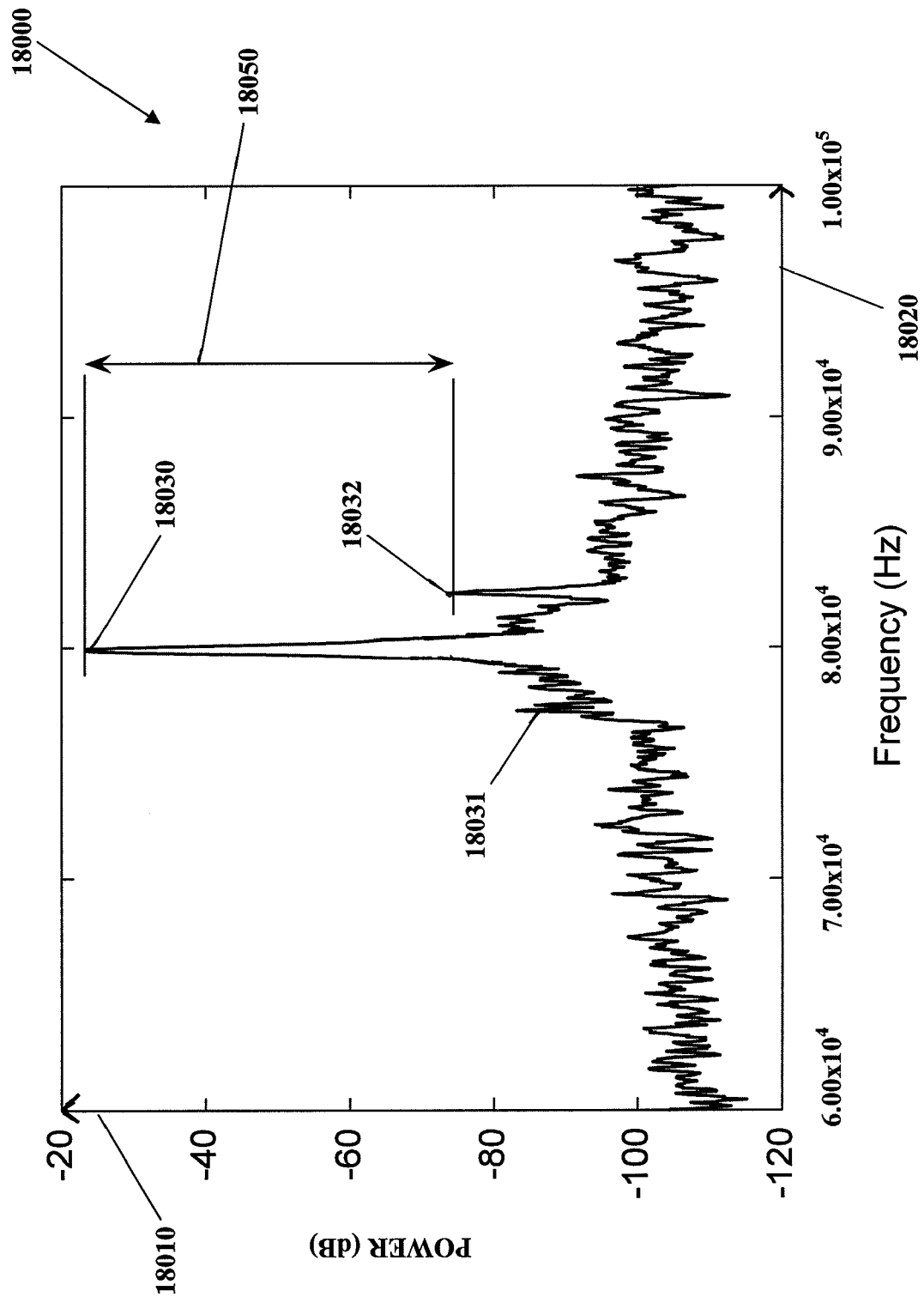
FIG. 18 shows a graph of frequency domain results of scanning a differentially encoded MD-class disk.

With reference to FIG. 18 there is shown graph 18000 with frequency increasing along its x axis as shown by x axis arrow 18020 and power spectrum increasing logarithmically along its y axis as shown by y axis arrow 18010. While the side bands off of DC yielded the best signal-to-noise ratio for scanning the MD-class disk described above in connection with FIG. 16, every carrier harmonic includes two side-bands. Thus, as shown in graph 18000 fundamental carrier harmonic 18030 which is at about 80 kHz includes sidebands 18031 and 18032. Sidebands 18031 and 18032 are small peaks above and below the harmonic carrier frequency 18030 which indicate the presence of the protein. Every other carrier harmonic also has two associated sidebands.

Figure 19:
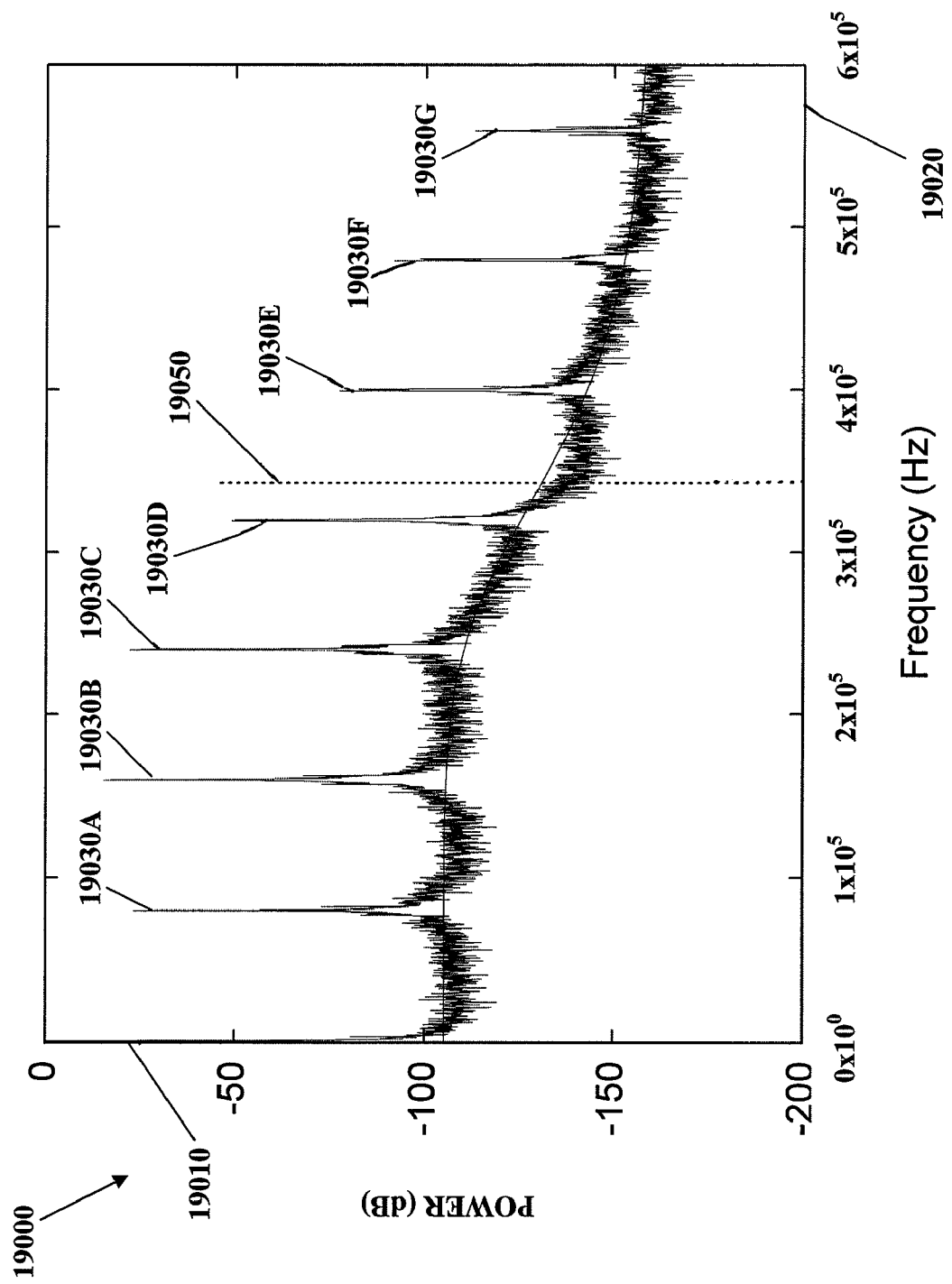
FIG. 19 shows a graph of frequency domain results of scanning a differentially encoded MD-class disk.

With reference to FIG. 19 there is shown graph 19000 with frequency increasing along its x axis as shown by x axis arrow 19020 and power spectrum increasing logarithmically along its y axis as shown by y axis arrow 19010. Graph 19000 shows carrier frequency harmonics 19030A (which is the first carrier harmonic 18030 at about 80 kHz described above in connection with FIG. 18), 19030B, 19030C, 19030D, 19030E, 19030F, and 19030G. Each carrier harmonic includes protein sidebands, though the wide frequency range of the graph 1900 makes it difficult to see the protein sidebands for all the harmonics. Graph 19000 also demonstrates the noise-floor roll-off for high frequencies associated to the transit time $t=w_0/v$ of a point on the disk across the width of the focused laser spot $w_o$. Line 19050 shows the approximate midpoint of the noise floor roll off.

Figure 20:
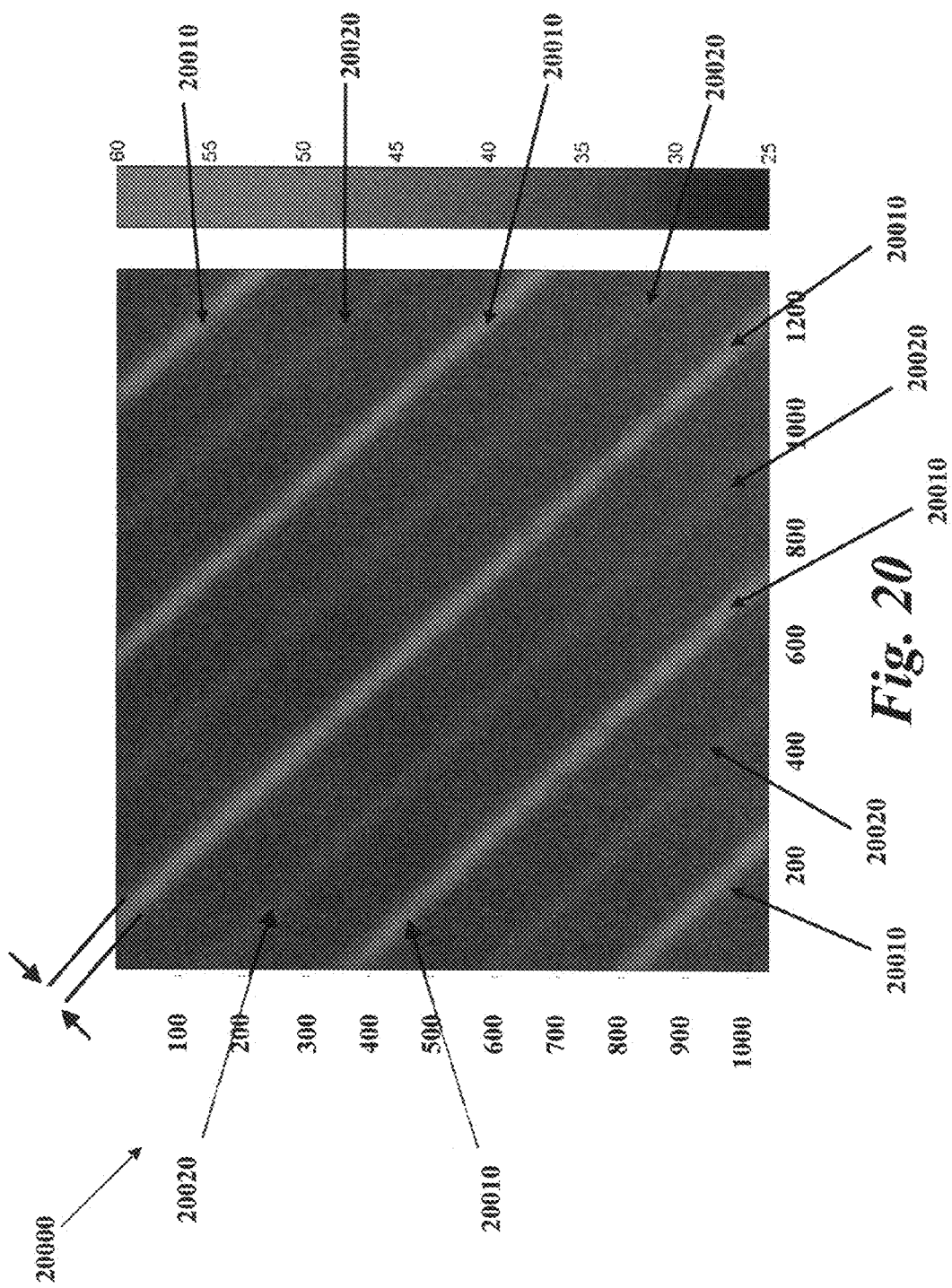
FIG. 20 shows a portion of an MD-class disk.

With reference to FIG. 20 there is shown a fluorescence microscope image of portion of an MD-class disk 20000 according to one embodiment of the present invention. Disk 20000 is a half-harmonic differentially encoded MD-class disk which was created using photolithography to immobilize protein on every alternating spoke. During this process half the spokes were covered by photo-patterned photoresist while the other half were exposed to protein. The photoresist was then removed to uncover bare gold spokes. This results in a disk where protein is immobilized on every alternating spoke as shown by lines 20010 (indicating deposition of specific antibody) and 20020 (indicating no deposition of antibody, or deposition of a non-specific antibody). The width of each protein deposit is about 20 microns as indicated by arrows SW. This half-harmonic differential encoding in which every alternating spoke carries protein results in the highest signal-to-noise ratio being attained. This provides for the highest-frequency differencing measurements, and also boosts the total protein signal when the zero-frequency upper sideband and the carrier frequency lower side-band merge into a single sideband half way between DC and the fundamental carrier frequency.

Figure 21:
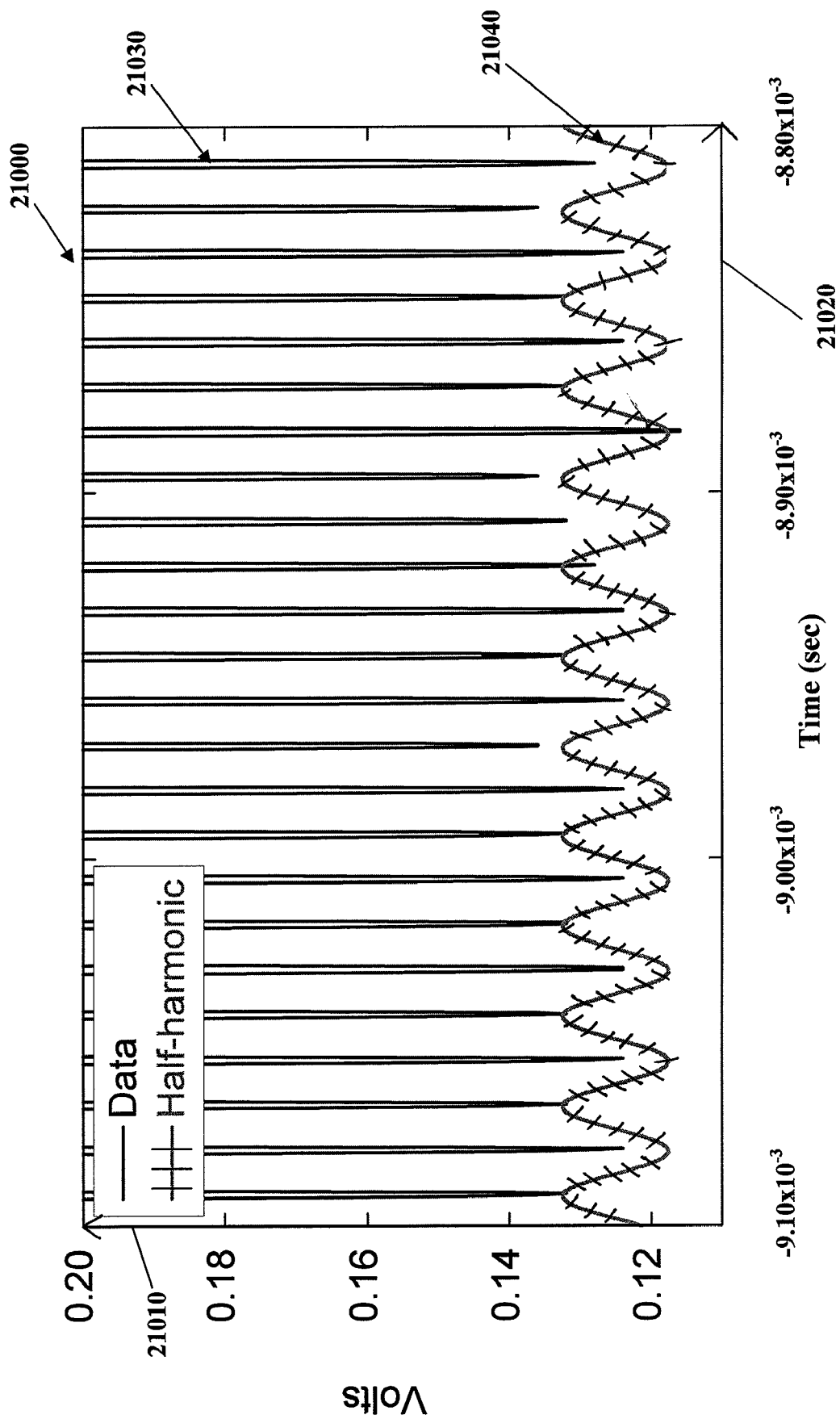
FIG. 21 shows a graph of time domain results of scanning the disk of FIG. 20.

With reference to FIG. 21 there is shown graph 21000 with time increasing along its x axis as shown by x axis arrow 21020 and voltage increasing along its y axis as shown by y axis arrow 21010. When a 512 differential encoded disk is rotated and scanned, the protein modulates the gold spokes with a frequency at half the fundamental carrier frequency. Graph 21000 shows the detected time trace 21030 from a 512 differential encoded disk. Trace 21030 shows an alternating pattern between the bare and protein-carrying spokes as indicated by the minimum points trace 21030 which alternate in amplitude at the rate of a half harmonic signal 21040.

Figure 22:
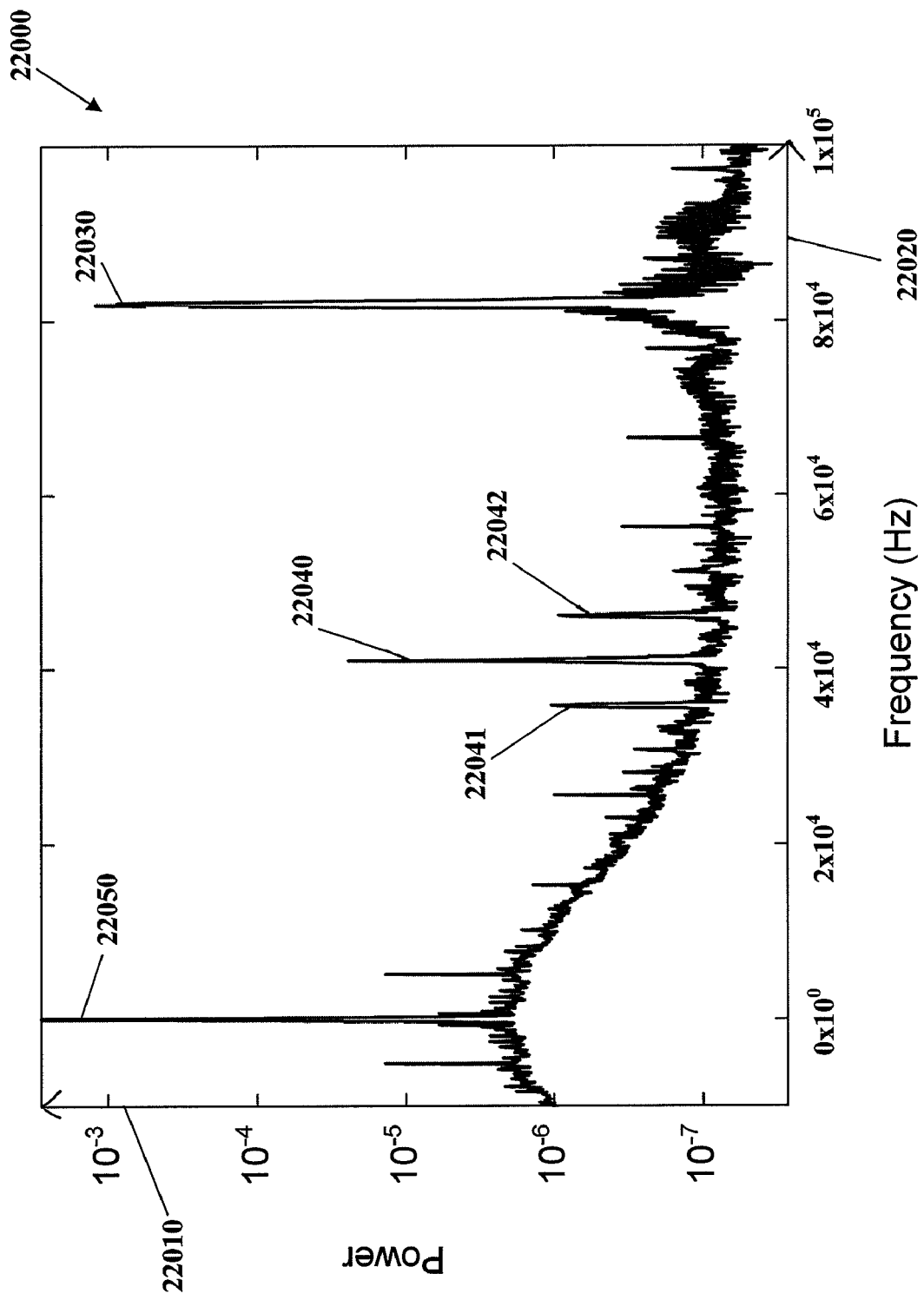
FIG. 22 shows a graph of frequency domain results of scanning the disk of FIG. 20.

With reference to FIG. 22 there is shown graph 22000 with frequency increasing along its x axis as shown by x axis arrow 22020 and power increasing logarithmically along its y axis as shown by y axis arrow 22010. Graph 22000 shows the frequency domain side band effect of the disk described above in connection with FIG. 21. The half-frequency harmonic protein signal 22040 is strong and occurs near the frequency of lowest noise between DC signal 22050 and the first carrier signal 22030. As shown in graph 22000 the DC sideband and first carrier sidebands have merged at the half-frequency harmonic protein signal 22040. Furthermore, the protein signal 22050 itself has sidebands 22041 and 22042 caused by slight asymmetries in the protein printing. The signal-to-noise ratio is greatest in this situation where the noise floor is lowest. Thus, detection of protein at signal 22040 represents the optimal performance condition for carrier sideband detection on the MD-class disk described above.

Figure 23:
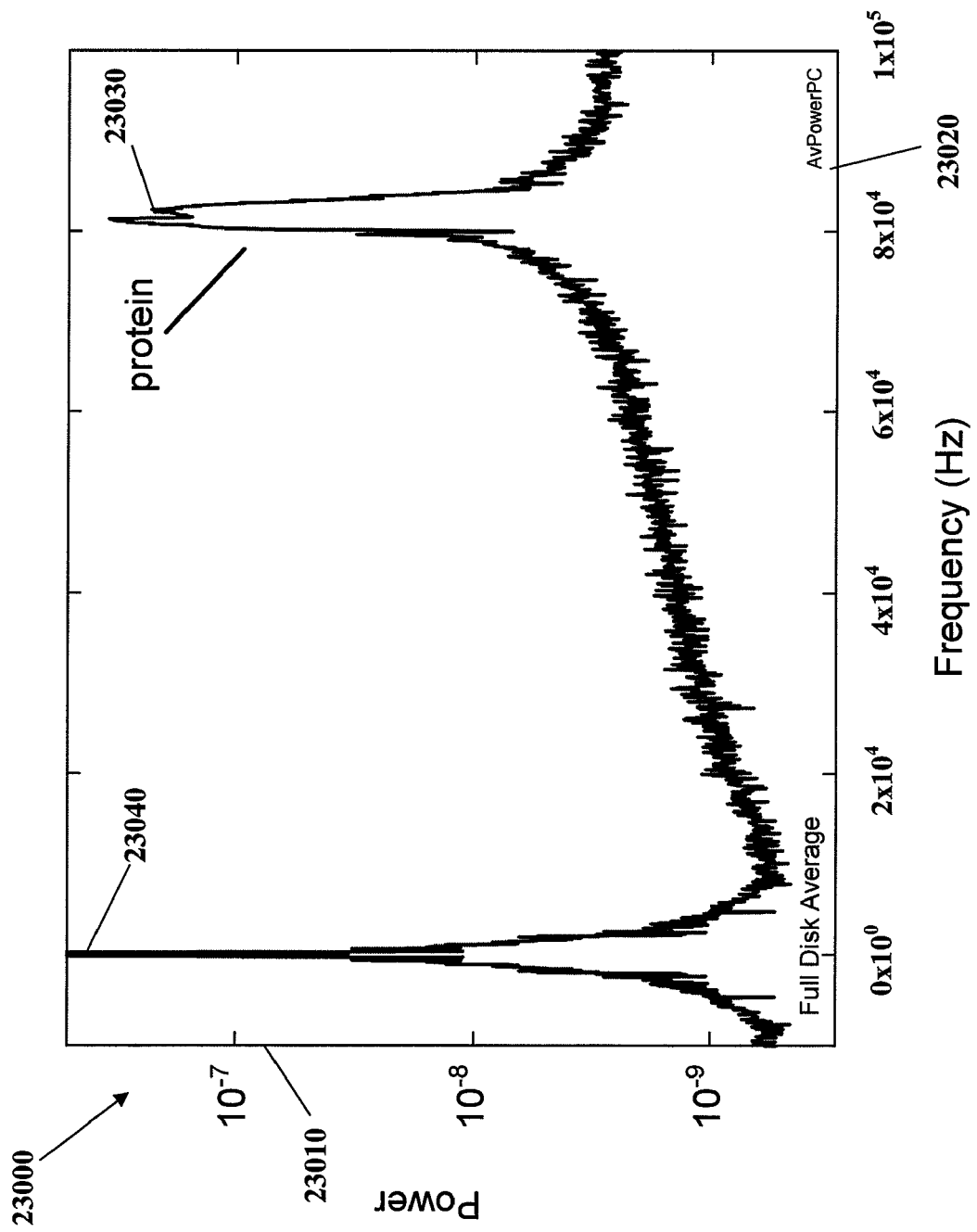
FIG. 23 shows a graph of time domain results of scanning a PC-class disk.

With reference to FIG. 23 there is shown graph 23000 with frequency increasing along its x axis as shown by x axis arrow 23020 and power spectrum increasing logarithmically along its y axis as shown by y axis arrow 23010. Graph 23000 shows the power spectrum for an embodiment of a PC-class disk with a periodic pattern of protein on a dielectric disk with no other disk structure. Graph 23000 shows DC signal 23040 and protein signal 23030 which is caused by and indicates the presence of protein. For this PC-class embodiment, the carrier frequency is attributable entirely to the protein, without any contribution from microstructures or other physical structures on the disk. The detection of periodic patterns of immobilized protein on a flat surface is one example of carrier-wave suppression that was discussed above. Additional embodiments including, for example, suppressing the carrier of the gold spokes on MD-class disks are also discussed above. Analyzer molecule patterns on PC-class disks offer a embodiment of side-band detection and manipulation that significantly improves the sensitivity of the bio-CD because the periodic protein patterns can themselves be modulated to form larger spatial patterns.

Figure 24:
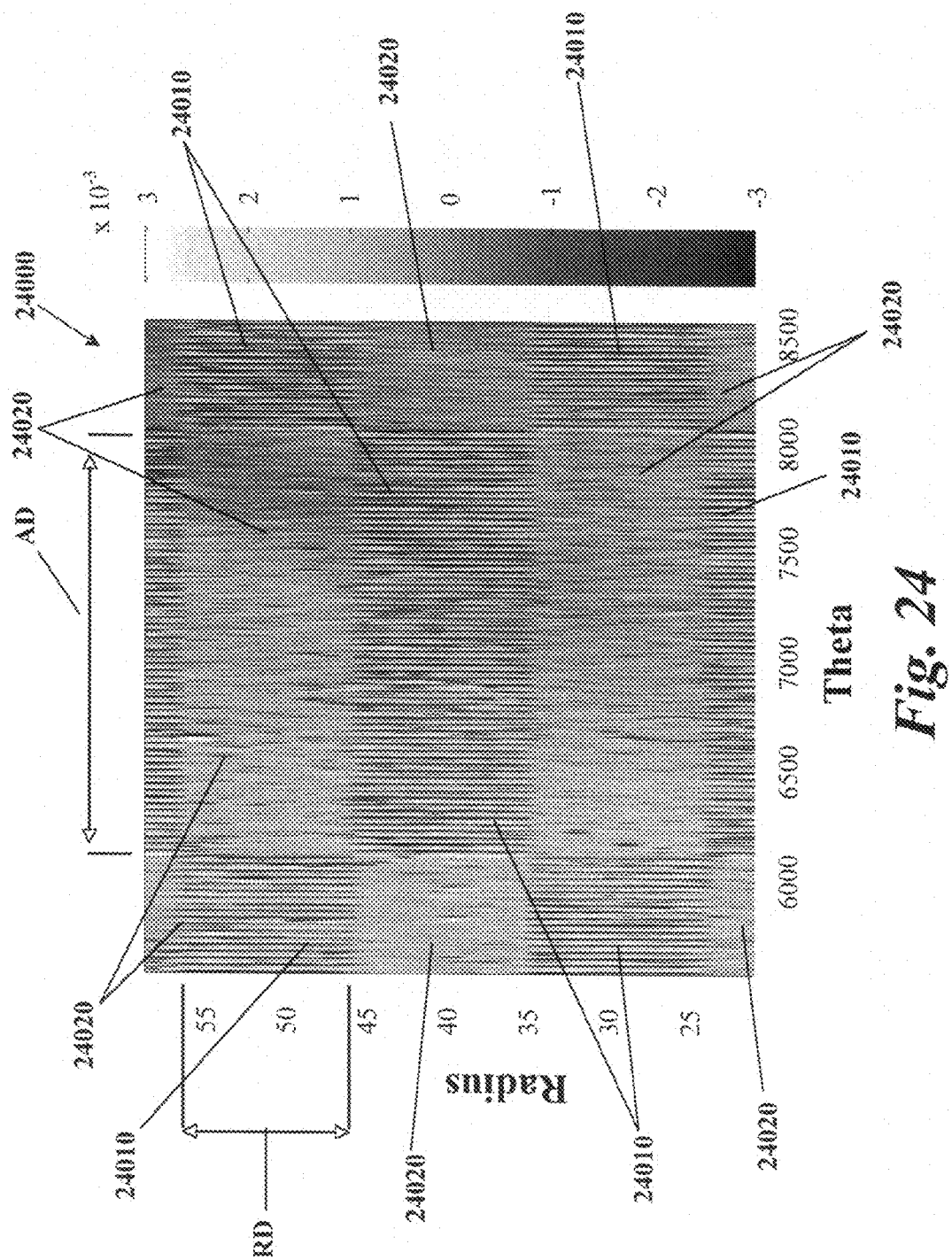
FIG. 24 shows a portion of a PC-class disk.

With reference to FIG. 24 there is shown a portion of a patterned protein PC-class disk 24000 according to one embodiment of the present invention. The radial direction is in the vertical direction the angular direction around the disk is in the horizontal direction. As shown in FIG. 11, the portion of disk 24000 is in a checkerboard pattern. Substantially rectangular areas of periodic stripes of protein 24010 are alternated with substantially rectangular areas of bare disk 24020. Each substantially rectangular area has a radial distance of approximately 0.5 mm indicated by arrow RD and an angular distance of approximately 45 degrees indicated by arrow AD. The height of the printed protein stripes is approximately 5 nm. The signal resulting from scanning the PC-class disk is differential, showing only the steps up and down from the protein stripes.

Figure 25:
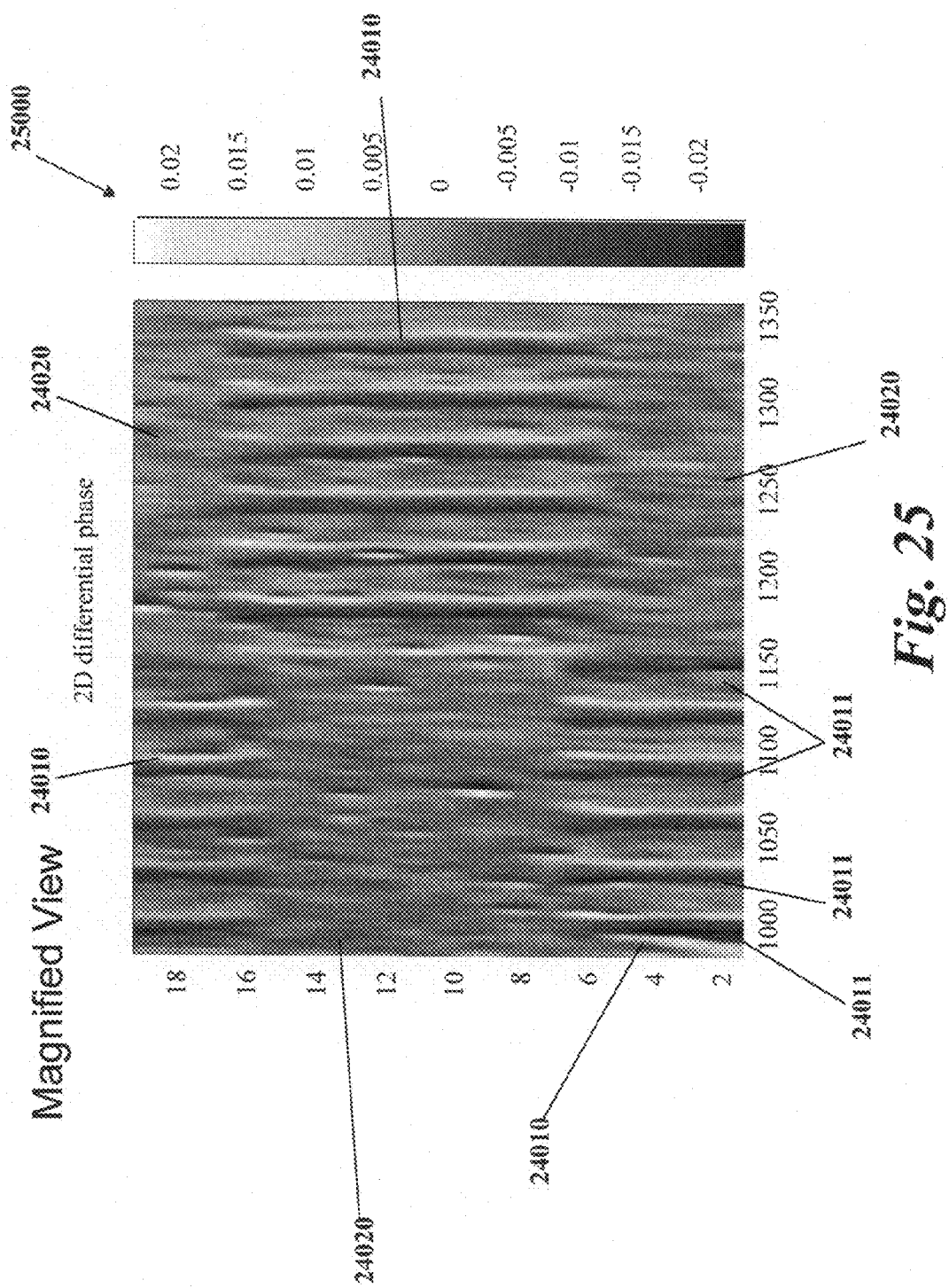
FIG. 25 shows a magnified view of a portion of FIG. 24.

With reference to FIG. 25 there is shown a magnified portion 25000 of the PC-class disk 24000 shown in FIG. 24 individual protein bands 24011 of protein regions 24010 are visible in magnified portion 25000. The rectangular spatial patterns of areas 24010 and 4020 of disk 24000 create sidebands on the protein peak in the power spectrum. The long-range spatial patterns can be detected using a sideband demodulation process conceptually similar to the demodulation of FM radio. The long-range protein patterns constitute an envelope that modulates the carrier wave. By demodulation, the envelope is extracted. Because it is more slowly varying, envelope demodulation makes it possible to perform more accurate prescan subtraction.

Figure 26:
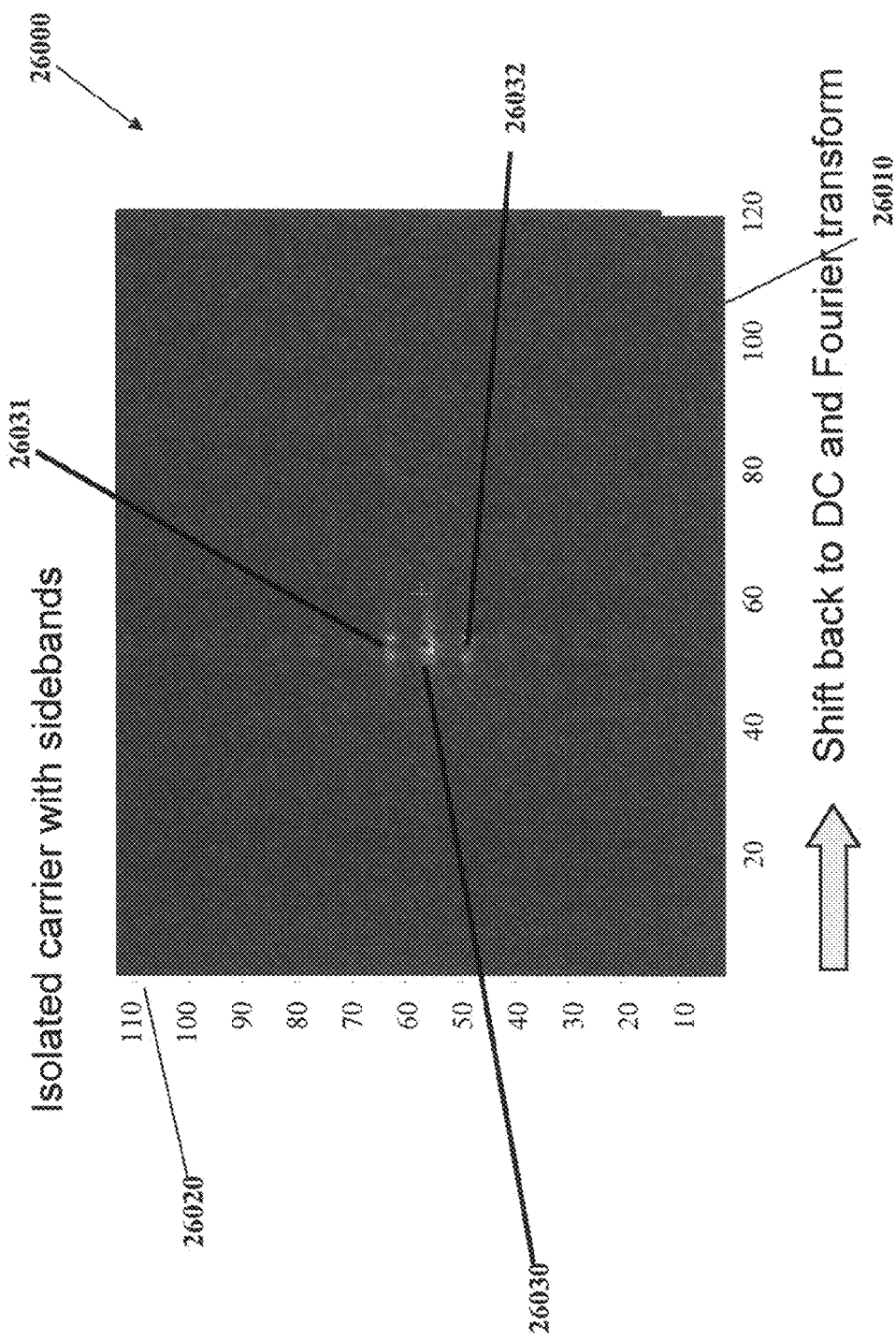
FIG. 26 shows Fourier domain results of scanning the disk of FIG. 24.
Figure 27:
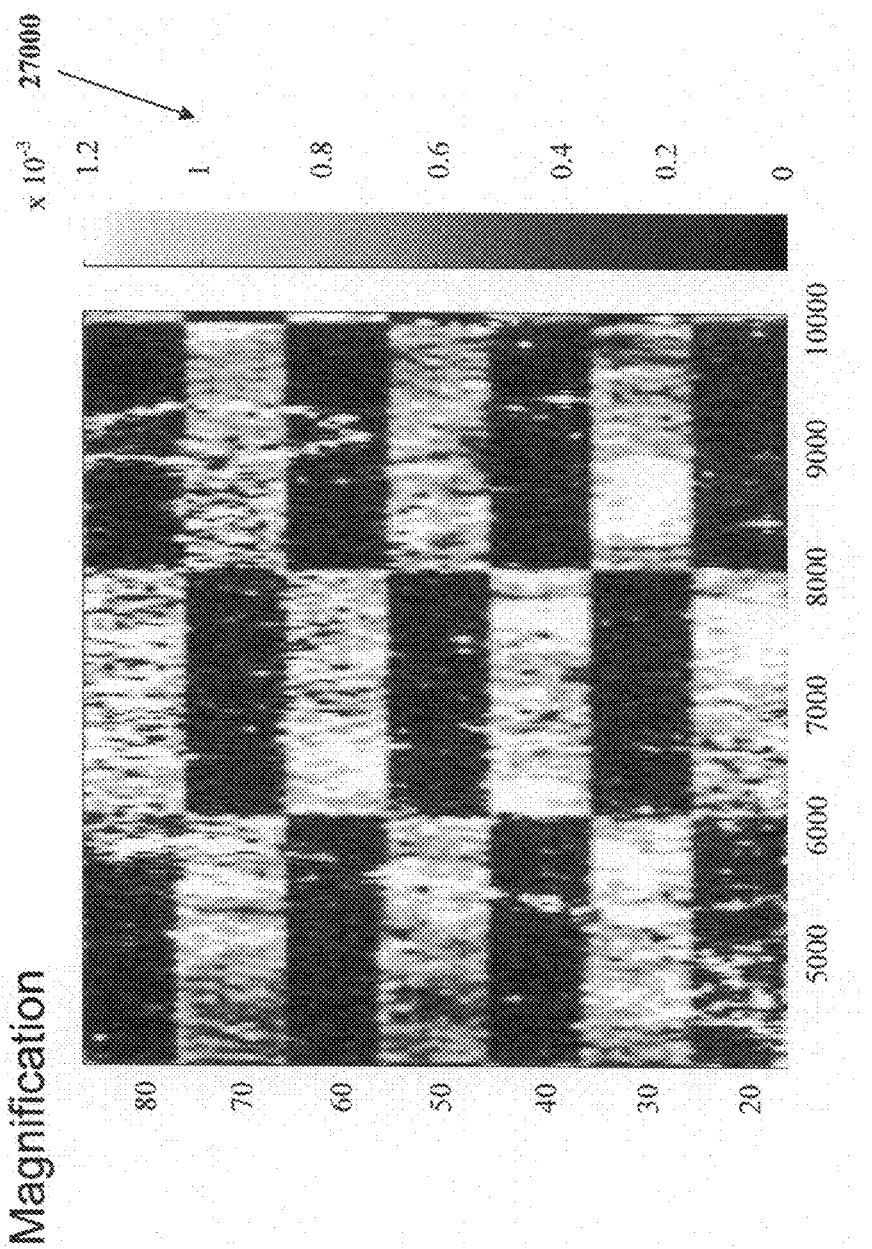
FIG. 27 shows a demodulated image of the of the Fourier domain results of FIG. 26.

An exemplary procedure for sideband detection will now be described with reference to FIGS. 26, 27 and 28. FIG. 26 shows an isolated protein peak 26030 in the power spectrum. The horizontal axis 26010 is temporal frequency and the vertical axis 26020 is spatial frequency along the radius of the disk. The sub-peaks 26031 and 26032 represent the long-range envelope pattern. To demodulate the signal and extract the protein envelope, this protein peak is shifted back to DC and then Fourier-transformed back into the space domain. The resulting demodulated image is shown in FIG. 27. Only the long-range checkerboard pattern 27000 corresponding to areas 24010 and 24020 is visible, with the periodicity of the individual protein bands 24011 removed. After demodulation, subtracting a prescan becomes much more accurate.

Figure 28:
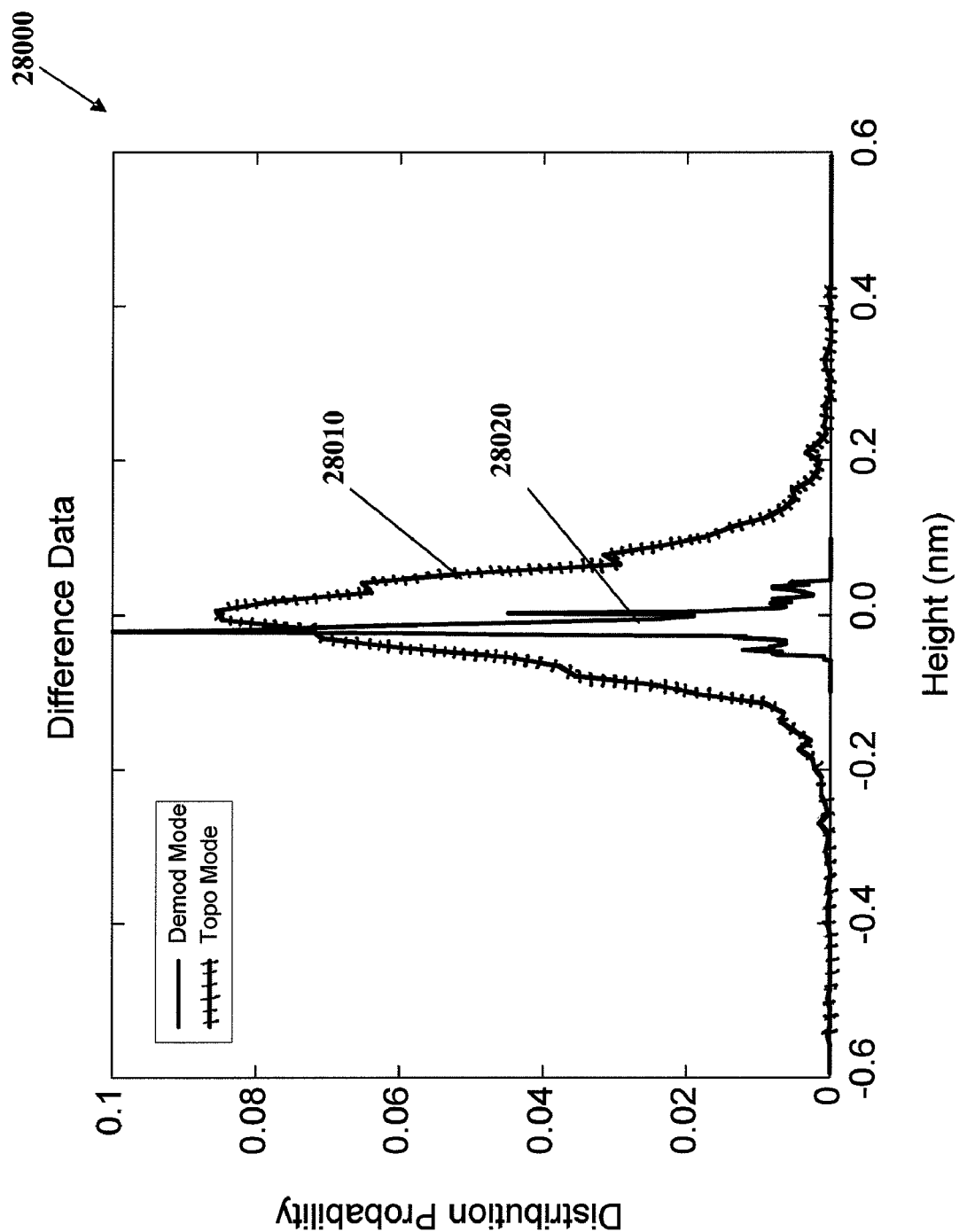
FIG. 28 shows a graph of a comparison of prescan subtraction without demodulation and prescan subtraction with demodulation.

FIG. 28 shows graph 28000 with distribution probability on the vertical axis and height in nm on the horizontal axis. Graph 28000 shows the results of subtracting a prescan from a postscan before demodulation as distribution 28010 and performing the same subtraction after demodulation as distribution 28020. The error in height reduces from 75 pm for distribution 28010 to 20 pm for distribution 28020 with demodulation. This increased accuracy improves surface mass sensitivity by over a factor of 3 in this example.

While the examples illustrated and described above in connection with FIGS. 14-28 have made reference to particular embodiments, for example, MD-class disks with protein attached using photolithographic techniques and PC-class disks with printed protein, these specific embodiments are merely exemplary and it is contemplated that differential encoding and sideband detection described above could be employed with a variety of other embodiments according to the present invention including those described elsewhere herein.

Various embodiments according to the present invention can include a variety of biosensor platforms including those described above. For example, these platforms include bio-CDs such as micro-diffraction bio-CDs, adaptive-optical bio-CDs, phase-contrast bio-CDs, and others. Details relating to these various classes of bio-CDs can be found, for example, in the aforementioned patents and patent applications. These platforms further include bio-chips, immunological chips, gene chips, DNA arrays, platforms used in connection with fluorescence assays and other platforms and substrates supporting planar arrays including analyzer molecules including, for example, those described herein.

Various embodiments according to the present invention can include a variety of analyzer molecules useful in detecting the presence or absence of a variety of target analytes in a solution to be tested. For example, these analyzer molecules can include antibodies or immunoglobulins, antigens, DNA fragments, cDNA fragments, aptameres, peptides, proteins, and other molecules. Various embodiments according to the present invention can include combinations of one or more of the foregoing and other types of analyzer molecules known to a person of ordinary skill in the art arranged, for example, in a planar array.

Various embodiments according to the present invention can be used in connection with a variety of scanning and detection techniques. For example, such techniques include interferometry, including surface normal interferometry techniques, and preferably phase quadrature interferometry techniques where one detected optical mode differs in phase from another by about $\pi/2$ plus or minus about twenty percent or an odd integer multiple thereof, and/or self referencing interferometry techniques where a reference wave is generated locally with respect to a signal wave so that the reference and signal waves experience common aberrations and path length changes and thus maintain a constant relative phase without the need for active stabilization of different light paths, florescence techniques and platforms, resonance techniques and platforms, and other techniques and platforms.

As used herein terms relating to properties such as geometries, shapes, sizes, physical configurations, speeds, rates, frequencies, periods, amplitudes, include properties that are substantially or about the same or equal to the properties described unless explicitly indicated to the contrary.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A method of detecting a target analyte in a test sample, the method comprising:

providing a substrate for supporting biological analyzer molecules, the substrate including at least one scanning pathway, locating a plurality of scanning targets along the scanning pathway, the plurality of scanning targets alternating periodically between a group of a first set of targets and a group of a second set of targets, the first set of targets including specific biological analyzer molecules adapted to detect the target analyte, and the second set of the targets not including the specific biological analyzer molecules;

contacting a test sample to the plurality of scanning targets;

scanning the plurality of scanning targets along the at least one scanning pathway at a rate to create a carrier frequency signal and sideband signals, the binding of the target analyte to the specific analyzer molecules of the first set of targets modulating the carrier frequency signal to create the sideband signals;

detecting the sideband signals; and determining the presence or absence of the target analyte in the test sample based on the sideband signals.

2. The method of claim 1, wherein the detecting step utilizes self referencing phase quadrature interferometric detection.

3. The method of claim 1, wherein the substrate is a bio-CD.

4. The method of claim 1, further comprising suppressing the carrier frequency signal.

5. The method of claim 1, wherein the detecting step utilizes interferometry and the scanning step utilizes a laser beam.

6. The method of claim 1, further comprising detecting the presence or absence of a second target analyte in the test sample, wherein detecting the second target analyte is based at least in part on the sideband signals.

7. The method of claim 1, wherein the detecting step includes detecting a harmonic signal closest to zero frequency.

8. The method of claim 1, wherein the detecting step includes detecting a harmonic signal at a frequency greater than that of a harmonic signal closest to zero frequency.

9. The method of claim 1, wherein the detecting step utilizes fluorescence detection to detect the sideband signals.

* * * * *